(12) United States Patent
Hsu et al.

(10) Patent No.: US 11,944,276 B2
(45) Date of Patent: Apr. 2, 2024

(54) SURGICAL DEVICES AND METHODS

(71) Applicant: Aulea Medical, Inc., San Ramon, CA (US)

(72) Inventors: George Chao-chih Hsu, San Ramon, CA (US); Csaba Truckai, Saratoga, CA (US)

(73) Assignee: Aulea Medical, Inc., San Ramon, CA (US)

( * ) Notice: Subject to any disclaimer, the term of this patent is extended or adjusted under 35 U.S.C. 154(b) by 0 days.

(21) Appl. No.: 17/531,565

(22) Filed: Nov. 19, 2021

(65) Prior Publication Data

US 2022/0322926 A1 Oct. 13, 2022

Related U.S. Application Data

(63) Continuation of application No. 16/184,844, filed on Nov. 8, 2018, now Pat. No. 11,272,835.

(Continued)

(51) Int. Cl.
*A61B 1/307* (2006.01)
*A61B 1/00* (2006.01)
(Continued)

(52) U.S. Cl.
CPC ............ *A61B 1/307* (2013.01); *A61B 1/0008* (2013.01); *A61B 1/00135* (2013.01);
(Continued)

(58) Field of Classification Search
CPC . A61B 1/00135; A61B 1/00154; A61B 17/34; A61B 17/3415; A61B 17/3417;
(Continued)

(56) References Cited

U.S. PATENT DOCUMENTS 5,354,302 A * 10/1994 Ko ..................... A61B 1/00087
604/161
5,752,970 A * 5/1998 Yoon .................. A61B 17/3498
604/167.03
(Continued)

FOREIGN PATENT DOCUMENTS

WO WO-2019094643 A1 5/2019

OTHER PUBLICATIONS

International Search Report and Written Opinion for PCT/US2018/059897 dated Jan. 17, 2019.
(Continued)

*Primary Examiner* — Ryan N Henderson
(74) *Attorney, Agent, or Firm* — Dorsey & Whitney LLP

(57) ABSTRACT

A medical introducer includes an elongated tubular member having a proximal end, a distal portion, and a central lumen extending from the proximal end to a distal port in the distal portion. A frame structure is coupled to the distal portion of the elongated tubular member, where frame structure supports the distal portion of the elongated tubular member in a tapered shape and alternatively in a non-tapered shape. The elongated tubular member may include a rigid outer tube and a rigid inner tube carried in an interior lumen of the outer tube. The distal portion is typically a reinforced elastomeric tubular extension of the outer tube, and the reinforced elastomeric tubular extension may have a conical shape.

12 Claims, 26 Drawing Sheets

Related U.S. Application Data

(60) Provisional application No. 62/584,550, filed on Nov. 10, 2017, provisional application No. 62/584,075, filed on Nov. 9, 2017.

(51) Int. Cl.
| | | |
|---|---|---|
| *A61B 1/005* | (2006.01) | |
| *A61B 18/14* | (2006.01) | |
| *A61B 90/11* | (2016.01) | |
| *A61B 17/00* | (2006.01) | |
| *A61B 17/32* | (2006.01) | |
| *A61B 17/34* | (2006.01) | |
| *A61B 18/00* | (2006.01) | |

(52) U.S. Cl.
CPC ........ *A61B 1/00154* (2013.01); *A61B 1/0058* (2013.01); *A61B 18/1482* (2013.01); *A61B 90/11* (2016.02); *A61B 2017/00274* (2013.01); *A61B 2017/00867* (2013.01); *A61B 2017/320028* (2013.01); *A61B 17/3417* (2013.01); *A61B 17/3439* (2013.01); *A61B 2018/00196* (2013.01); *A61B 2018/00208* (2013.01); *A61B 2018/00291* (2013.01); *A61B 2018/00517* (2013.01); *A61B 2018/00547* (2013.01); *A61B 2018/00601* (2013.01); *A61B 2018/00982* (2013.01); *A61B 2018/144* (2013.01); *A61B 2218/002* (2013.01); *A61B 2218/007* (2013.01)

(58) Field of Classification Search
CPC ............ A61B 17/3421; A61B 17/3423; A61B 17/3431; A61B 17/3439; A61B 2017/3425; A61B 2017/3427; A61B 2017/3429; A61B 2017/3433; A61B 2017/3435; A61B 2017/3437; A61B 2017/3441; A61B 2017/3443; A61B 2017/3445; A61B 2017/3447; A61B 2017/3449; A61B 1/00142; A61B 1/0008; A61B 1/00089; A61B 1/00101; A61M 25/0023; A61M 2025/0024; A61M 2025/0035

See application file for complete search history.

(56) References Cited

U.S. PATENT DOCUMENTS

| | | | | |
|---|---|---|---|---|
| 5,824,002 A * | 10/1998 | Gentelia | ............ | A61B 17/3417 604/164.11 |
| 6,358,238 B1 * | 3/2002 | Sherry | ................ | A61M 25/005 604/524 |
| 6,508,825 B1 * | 1/2003 | Selmon | ................ | A61M 29/02 606/198 |
| 6,537,288 B2 * | 3/2003 | Vargas | ............. | A61B 17/32053 606/153 |
| 6,770,026 B2 * | 8/2004 | Kan | ................. | A61B 17/0218 600/114 |
| 6,939,318 B2 * | 9/2005 | Stenzel | ............. | A61B 17/3468 604/60 |
| 7,056,329 B2 * | 6/2006 | Kerr | .................. | A61B 17/3496 606/190 |
| 7,604,648 B2 * | 10/2009 | Kerr | .................. | A61B 17/0206 606/198 |
| 8,262,619 B2 * | 9/2012 | Chebator | .......... | A61M 25/0668 604/164.05 |
| 8,337,394 B2 * | 12/2012 | Vakharia | ............ | A61B 1/00135 600/114 |
| 9,056,182 B2 * | 6/2015 | Moulton | .......... | A61M 25/0074 |
| 9,308,077 B2 * | 4/2016 | Behan | .................. | A61F 2/2476 |
| 9,980,715 B2 * | 5/2018 | Marino | ................. | A61F 2/0811 |
| 10,004,556 B2 | 6/2018 | Orczy-Timko et al. | | |
| 10,736,491 B2 | 8/2020 | Truckai | | |
| 10,939,933 B2 | 3/2021 | Truckai | | |
| 11,272,835 B2 | 3/2022 | Hsu et al. | | |
| 2002/0042622 A1 * | 4/2002 | Vargas | ................... | A61F 2/064 606/153 |
| 2004/0073088 A1 | 4/2004 | Friedman et al. | | |
| 2004/0082969 A1 * | 4/2004 | Kerr | .................... | A61B 17/0218 606/205 |
| 2007/0051375 A1 * | 3/2007 | Milliman | ........... | A61B 17/0218 128/856 |
| 2007/0244440 A1 * | 10/2007 | Pal | ..................... | A61M 25/0074 604/164.13 |
| 2008/0097476 A1 * | 4/2008 | Peh | ......................... | A61B 1/04 606/130 |
| 2008/0161902 A1 * | 7/2008 | Poulsen | .................... | A61F 2/95 623/1.11 |
| 2010/0081877 A1 * | 4/2010 | Vakharia | ............... | A61B 1/3132 600/129 |
| 2011/0160539 A1 * | 6/2011 | Robertson | .......... | A61B 17/3421 600/204 |
| 2012/0083740 A1 * | 4/2012 | Chebator | ........... | A61M 25/0074 604/164.03 |
| 2012/0323180 A1 * | 12/2012 | Chebator | ........... | A61M 25/0668 604/164.03 |
| 2014/0200398 A1 * | 7/2014 | Hawkins | ........... | A61B 17/12172 600/37 |
| 2014/0236088 A1 | 8/2014 | Al-Rashdan et al. | | |
| 2014/0236122 A1 | 8/2014 | Anderson et al. | | |
| 2015/0250992 A1 * | 9/2015 | Morriss | ............. | A61M 25/0074 606/198 |
| 2016/0106562 A1 * | 4/2016 | Puckett, Jr. | ............. | A61F 2/966 606/108 |
| 2016/0228116 A1 * | 8/2016 | Milliman | ........... | A61B 17/3431 |
| 2016/0235279 A1 * | 8/2016 | Yamakawa | ........ | A61B 1/00154 |
| 2017/0014252 A1 * | 1/2017 | Kelly | ................. | A61M 25/0068 |
| 2017/0035274 A1 * | 2/2017 | Mikkaichi | ................ | A61B 1/00 |
| 2017/0105507 A1 | 4/2017 | Golding et al. | | |
| 2017/0265892 A1 * | 9/2017 | Winegar | ........... | A61B 17/3415 |
| 2017/0333119 A1 | 11/2017 | Truckai | | |
| 2017/0333120 A1 | 11/2017 | Truckai | | |
| 2018/0036156 A1 * | 2/2018 | Kelly | .................. | A61B 17/3468 |
| 2018/0221054 A1 | 8/2018 | Truckai | | |
| 2018/0020077 A1 | 10/2018 | Benedek et al. | | |

OTHER PUBLICATIONS

Office action dated Apr. 11, 19 for U.S. Appl. No. 16/184,844.
Office action dated Oct. 10, 19 for U.S. Appl. No. 16/184,844.
Office action dated Nov. 27, 20 for U.S. Appl. No. 16/184,844.
U.S. Appl. No. 16/184,844 Notice of Allowance dated Aug. 16, 2021.

\* cited by examiner

SURGICAL DEVICES AND METHODS

BACKGROUND OF THE INVENTION

This application is a continuation of U.S. patent application Ser. No. 16/184,844, filed Nov. 8, 2018, which claims the benefit of provisional patent application No. 62/584,075, filed on Nov. 9, 2017, and of provisional patent application No. 62/584,550, filed on Nov. 10, 2017, the full disclosures of which are incorporated herein by reference.

BACKGROUND OF THE INVENTION

1. Field of the Invention

The present invention relates to devices and methods for resecting and removing tissue from an interior of a patient's body, for example in a transurethral resection of prostate tissue to treat benign prostatic hyperplasia.

Electrosurgical cutting devices often comprise a shaft or sleeve having a tissue extraction lumen with one or more radio frequency (RF) cutting blades arranged to resect tissue which may then be drawn into the extraction lumen, often via vacuum assistance through a cutting window. Most such electrosurgical tissue cutting devices rely on manually engaging the cutting window against the target tissue to be resected. While such manual engagement is often sufficient, in other cases, such as in laparoscopic procedures having limited access and field of view, the target tissue can be difficult to visualize prior to resection and, in particular, it can be difficult to assure that the optimum target site has been engaged by the cutting window. For these reasons, it would be desirable to provide improved electrosurgical cutting tools having improved visibility and ability engage and immobilize tissue prior to cutting and to extract the tissue from tools after cutting.

For resection of remote tissue sites, such as the prostate, it is usually desirable to introduce the surgical cutter through a tubular introducer device. Though such tubular introducers can be advanced "blind," i.e., without direct optical visualization, it is frequently advantageous to provide such introducers with direct visualization. For example, it would be desirable to use an endoscope to observe the urethra while transurethrally advancing an introducer sheath for subsequent resection of the prostrate. Once the introducer sheath is in place and the surgical cutter has been introduced, however, it will still be necessary to move a cutter element on the surgical cutter to resect the tissue. Heretofore, this has typically been accomplished by manually reciprocating a cutter assembly on the tissue resecting apparatus. Manual resection, while generally effective, can be difficult to control and, in particular, can be difficult to coordinate with other aspects of the resection procedure, such as applying RF power, applying a vacuum to aspirate tissue fragments and debris, and the like.

For these reasons, it would be desirable to provide improved apparatus, systems and methods for resecting tissue in prostatectomies and other procedures. It would be particularly desirable to provide apparatus, systems and methods which provide improved control of tissue resection including but not limited to enhanced coordination of cutter movement control, cutting power control, vacuum aspiration control, and the like. At least some of these objectives will be met by the inventions described below.

2. Description of the Background Art

Commonly owned patents and published applications include U.S. Pat. No. 10,004,556; US 2018-0280077; US 2018-0221054; US 2017-0333119; US 2017-0333120; US 2017-0105607; and US 2017-0105748.

SUMMARY OF THE INVENTION

Figure 1:
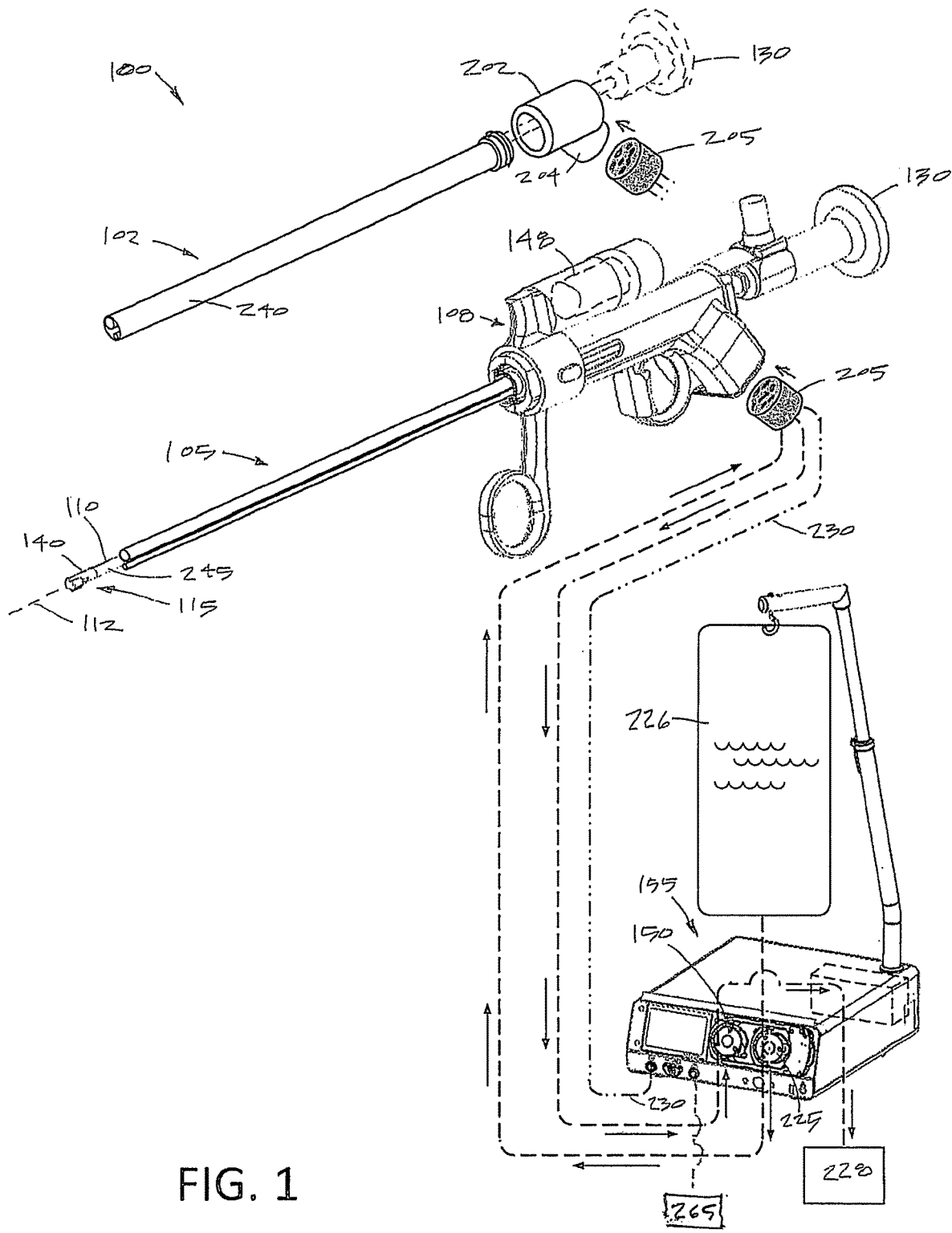
FIG. 1 is a view of a tissue resecting device and a block diagram of systems and operating components corresponding to the invention.

The present invention provides apparatus, systems, and methods for performing electrosurgical resections in minimally invasive procedures. While the apparatus, systems, and methods are particularly suitable for performing transurethral resection of the prostate (often referred to as TURP), they will also find use in a variety of other laparoscopic and other endoscopic and endosurgical procedures. The apparatus comprises motor-driven cutters, where the motors are configured to drive both a shaft of the cutter and a cutter electrode, either independently, contemporaneously, or selectively independently and contemporaneously. The systems comprise the cutters together with a digital or other controller configured to coordinate movements of the shaft, electrodes, and other external components such as a radiofrequency power supply (e.g. by selecting a cutting or a coagulation waveform, power, timing, etc.), a negative pressure source, and the like. The methods of the present invention comprise using the apparatus and systems as just described for prostatectomies and other tissue resection procedures.

In a first aspect, the present invention provides a tissue resecting device comprising a shaft assembly movably attached to a handle and having a longitudinal axis. A housing is secured to a distal end of the shaft and has a window configured to be fluidly coupled to a negative pressure source. An electrode is disposed in the housing and configured to move relative to the window, and at least one motor in the handle is adapted to both (1) move the shaft assembly in an axial stroke relative to the handle and (2) move the electrode across the window.

In specific embodiments and examples of the tissue resecting device, the at least one motor is adapted to move the shaft assembly and the electrode contemporaneously, i.e. at the same time. In other specific embodiments and examples, the at least one motor is adapted to selectively move either the shaft assembly or the electrode individually. In many embodiments, the at least one motor will be adapted to move the shaft assembly and electrode both contemporaneously and individually at different times during a procedure. In still additional specific examples, the motor will be adapted to move the electrode at a fixed speed or rate relative to the window, e.g. at a rate greater than 1 cycle per second (CPS), often greater than 5 CPS. The motor may be still further adapted to reciprocate the shaft assembly at a rate greater than once every two seconds, frequently at a rate greater than once every second.

The shaft and/or the electrode may be operated manually and/or automatically. That is, the user may be able to manually initiate the at least one motor to move the electrode in the housing relative to the window and/or to manually activate the at least one motor to reciprocate the shaft in an axial stroke relative to the handle. Even when being operated manually, the tissue resecting device will usually be operated through an interface (typically including a radiofrequency (RF) power supply) which may provide for specific operational parameters, often fixed or manually adjustable parameters, such as stroke times, power levels, RF waveforms, and the like, without having feedback control capability.

Often, however, the tissue resecting device will be provided as part of a tissue resecting system which further comprises a controller which is configured to operate not only the motor, but usually also a RF power source which is coupled to the electrode and also a negative pressure source which may be coupled to the window in the housing. The controller may be further configured or adapted to automatically or manually control at least one motor to stop movement of the electrode in a selected position relative to the window. Alternatively or additionally, the controller may be adapted to stop the electrode in the center of the window. Alternatively or additionally, the controller may be adapted to stop the electrode at an end of the window.

The controller may be adapted in a variety of other different control protocols. For example, the controller may be adapted to control the at least one motor to provide a single movement cycle of the electrode back and forth across the window. That is, the user may be able to cause the controller to initiate only a single pass of the electrode over the window in order to achieve a controlled cutting of tissue. In other instances, the controller may be adapted to control the at least one motor to stop axial movement of the shaft in a selected axial position. The controller may be further adapted to control the at least one motor to provide a single movement of the shaft in retracting and/or extending stroke.

Additionally, the controller will usually be configured to control and coordinate the delivery of negative pressure from the negative pressure source to the housing window and to actuate the at least one motor, usually contemporaneously.

In still other aspects of the control systems of the present invention, the controller may be configured to modulate the negative pressure source in response to movement of the shaft assembly. That is, the negative pressure may be applied only, for example, when the shaft is extend and/or may be deactivated only when the shaft is retracted.

In still further aspects of the systems of the present invention, the controller may be configured to modulate the negative pressure source in response to movement of the electrode relative to the window. For example, the controller may be configured to active or deactivate the RF source in response to movement of the electrode relative to the window. Still additionally, the controller may be configured to activate or deactivate the RF source to deliver a cutting current waveform or a coagulation waveform to the electrode.

In a second aspect, a tissue resecting system comprises a handle, an elongate shaft, an electrode, and a controller. The elongate shaft is reciprocally connected to the handle and extends along a longitudinal axis to a working end. The working end is movable in a stroke between a first axial position and a second axial position relative to the handle. The electrode is disposed at the working end of the shaft and is configured to be coupled to an RF source. An aspiration channel is formed in the elongate shaft and communicates with a window in the working end of the shaft and is configured to be coupled to a negative pressure source. The controller is operatively connected to the RF source and the negative pressure source and is configured to modulate energy delivery from the RF source to the electrode and to modulate negative pressure to the aspiration channel where modulations of both pressure and energy are in response to an axial position of the working end in said stroke.

In a third aspect, a method of the present invention for resecting tissue comprises providing an elongate shaft assembly. The elongate shaft assembly includes an electrode proximate a window in a housing. A motor reciprocates the shaft assembly in a retracting stroke and an extending stroke relative to a handle. The handle is manipulated to position the electrode against a targeted tissue site, and a negative pressure source may be activated to communicate with the window in the working end to draw tissue to or through the window. The RF source is then activated to deliver RF current to the electrode, and the motor is controlled to reciprocate the shaft assembly in a retracting stroke to resect tissue. Optionally, the motor may further laterally reciprocate or otherwise drive the electrode in a lateral stroke across the window to effect tissue resection.

In specific embodiments and examples, the steps of activating the negative pressure source, activating the RF source, and controlling the motor are performed by a digital or other controller. The methods may further comprise deactivating the negative pressure source at the proximal end of the retracting stroke. The methods may alternatively or additionally comprise deactivating the RF source at the proximal end of the retracting stroke. The methods may still further alternatively or additionally comprise commencing the extending stroke with the negative pressure source deactivated, commencing the extending stroke with the RF source deactivated, activating the negative pressure source during a portion of the extending stroke, and/or activating the negative pressure during a terminal portion of the extending stroke.

In particular aspects of the present invention as described in detail below, the devices, systems and methods are particularly configured for treating the prostate, optionally under endoscopic visualization. For example, the systems may comprise a RF source configured to deliver RF current alternatively in a cutting waveform and a coagulation waveform to the electrode, a motor configured to move the electrode, and a controller configured to operate the motor and RF source in a first mode delivering a cutting waveform while activating the motor to move the electrode and in a second mode delivering a coagulation waveform after de-activating the motor to stop the electrode in a selected stationary position. Such methods for treating the prostate may comprise providing a treatment device with a shaft extending along a longitudinal axis to a distal portion having a window communicating with an aspiration source and a motor driven electrode adapted to move relative to the window. The window is engaged against targeted prostate tissue, and the RF source is operated in a first mode with a cutting waveform delivered to the electrode while activating the motor to move the electrode to resect tissue and thereafter operated in a second mode with a coagulation waveform delivered to the electrode after de-activating the motor to stop the electrode in a selected stationary position to coagulate tissue.

In another aspect of the present invention, a medical device comprises an elongated tubular member having a proximal end, a distal portion, and a central lumen extending from the proximate end to a distal port in the distal portion. A frame structure is coupled to the distal portion of the elongated tubular member and is configured to support the distal portion in each of a tapered shape and a non-tapered shape. In specific instances, the tapered shape may be conical (typically frusto-conical with an open port defining a narrow, distal end) and the non-tapered shape may be cylindrical. Other tapered shapes, such as a rounded-nose shape, a pyramidal shape, hemispherical, funnel-like, and the like, as well as other non-tapered shapes, such as those having ellipsoidal, polygonal, and other cross-sectional geometries, may also find use.

In other specific instances, the frame structure may be configured to open the distal portion of the elongated tubular member to its non-tapered shape in response to an internal, radially outwardly acting force (such as that applied by advancing a tubular or other structure distally through a lumen of the distal portion) and to resiliently close the distal portion to its tapered shape in the absence in such an internal, radially outwardly acting force.

The frame structure will often comprise struts which are embedded in an elastomeric region of the distal portion of the elongated tubular member, where the struts may have a variety of specific configurations, including zig-zag, serpentine, axially oriented, and the like. In still other instances, the elastomeric material may be substantially transparent to allow better visualization of instruments and tools being introduced through the medical device.

In still further specific examples, the elongated tubular member may comprise an outer tube and an inner tube carried in an interior lumen of the outer tube. The inner tube may be configured to axially translate from (a) an axially retracted position wherein the frame structure is resiliently closed and the distal portion of the elongated tubular member is in its tapered shape to (b) an axially extended position where the frame structure is open and the distal portion is in its non-tapered state.

In other specific examples and embodiments, the interior lumen of the elongated tubular member transitions to a central passageway in the distal portion of the elongate tubular member and extends to the distal port. The central passageway in the distal portion will typically taper to a distal port having a diameter less than a diameter of the interior lumen proximal of the distal portion when said distal portion is in its tapered shape. Similarly, the central passageway in the distal portion will typically have a constant diameter equal to a diameter of the interior lumen proximal of the distal portion when the distal portion is in its non-tapered shape.

In yet other instances and embodiments, the elongated tubular member may comprise a rigid outer tube and a rigid inner tube carried in an interior lumen of the outer tube. In such instances, the distal portion may comprise a reinforced elastomeric tubular extension of the outer tube which will often have a conical shape.

In still other examples and instances, the frame structure may comprise a shape memory material having a conical shape memory (i.e. when in its unstressed condition) and expandable to a cylindrical shape when subjected to an internally applied, radially outwardly oriented force. The shape memory material may be formed into a variety of geometries, such as a zig-zag ring, a serpentine ring, a plurality of axial struts joined to a base ring, a plurality of unconnected axial struts, a plurality of axially extending rings attached to a distal end of the outer tube, and the like.

The central lumen of the elongated tubular member may be configured in a variety of ways for a variety of purposes. For example, the central lumen may be configured to accommodate an endoscope, an elongated shaft of a treatment device, or for a variety of other purposes. In still other instances, the elongated tubular member may be configured to be connected to a negative pressure source. In such instances, the negative pressure source may be specifically configured to connect to an annular space between an inner surface of the outer tube and an outer surface of the inner tube, where the outer tube is usually perforated allowing aspiration through such perforations.

The tubular member may be still further configured for other specific purposes. For example, the tubular member may include an interior channel communicating with the fluid inflow source and/or an inner channel communicating with a pressure sensor. The medical device may further comprise an actuator for moving the inner tube between a retracted and extended position relative to the outer tube.

In yet another aspect of the present invention, a medical introducer comprises an outer tube having a proximal end, a distal end, and a lumen therebetween. An elastomeric sleeve extends distally from the distal end of the outer tube, where the elastic sleeve usually tapers in a distal direction from the distal end of the outer tube to a distal port. A concentric inner tube is slidably received in the lumen of the outer tube, where the inner tube is configured to move between a retracted position and an extended position. In its retracted position, the inner tube does not engage the elastomeric sleeve which is able to remain in its tapered configuration. In contrast, when extended, the inner sleeve engages the elastomeric sleeve to open the elastomeric sleeve to its non-tapered shape.

In specific instances, the elastomeric sleeve structure includes reinforcement configured to inhibit axial stretching as the inner tube is moved between its retracted and extended positions. The reinforcement structure may take a variety of forms, such as deformable struts coupled to a distal end of the outer tube. In such instances, the deformable struts are typically metal. In still other instances, the reinforcement may comprise ribs molded into the elastomeric sleeve. In such instances, the distal port and the elastomeric sleeve may be concentrically aligned with a central axis of the outer tube. Alternatively, the distal port and the elastomeric sleeve may be radially offset from the central axis of the outer tube.

In still further aspects of the present invention, systems comprising any of the medical introducers described above may be combined with a tool configured to be introduced through a lumen of the concentric inner tube. For example, the tool may be an endoscope, an RF tool, or the like. The systems may further comprise a fluid source connectible to a lumen of the inner tube. The systems may still further comprise a negative pressure source connectible to an annular space between the outer tube and the inner tube of the specific embodiments of the medical introducer described above.

In a still further aspect of the present invention, a medical introducer comprises an outer tube having a proximal end, a distal end, and a lumen therebetween. A tapered elastomeric sleeve extends distally from the distal end of the outer tube, and a circumferentially expandable elastomeric sleeve is disposed on the outer tube proximally of the tapered elastomeric sleeve. A concentric inner tube is configured to move between a retracted and an extended position relative to the outer tube. When in its extended position, the inner sleeve will deform the tapered elastomeric sleeve structure outwardly into a cylindrical shape.

DETAILED DESCRIPTION OF THE INVENTION

FIG. 1 illustrates an electrosurgical tissue resecting system 100 for use in urological procedures to resect tissue that includes an introducer sleeve or sheath 102 and a hand-held single-use tissue resecting device or probe 105. The resecting device 105 has a handle portion 108 that is coupled to an elongated shaft or extension portion 110 that has an outer diameter ranging from about 2 mm to 7 mm, and in one variation is 5 mm in diameter. The shaft 110 extends about longitudinal axis 112 to a working end 115 that is radially asymmetric relative the shaft 110 and its axis 112 as further described below. In one variation, the device is adapted for performing a TURP procedure (transurethral resection of prostate) or a bladder tumor resection procedure and thus the shaft portion 110 extends about axis 112 with a length suitable for introducing in a transurethral approach to reach the targeted prostate tissue or bladder tissue.

As will be described below and shown in FIG. 1, the resecting device 105 is adapted for introduction through the introducer sleeve 102. Such an introducer sleeve 102 is adapted to receive a commercially available endoscope 130 as can be understood from FIG. 1.

Figure 2:
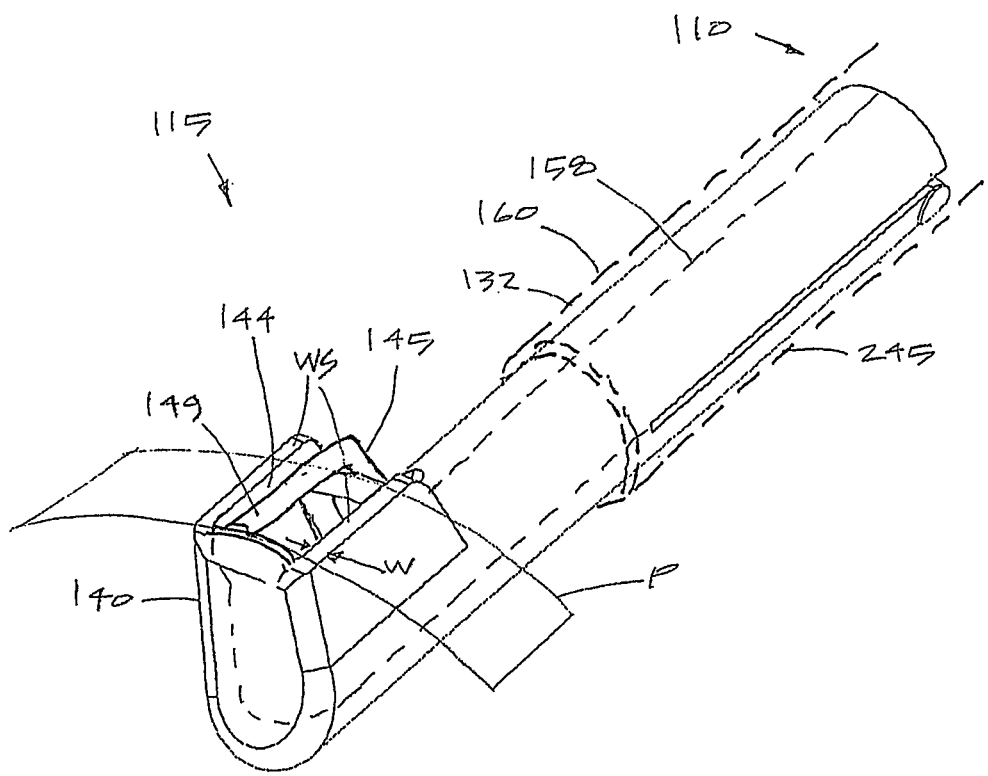
FIG. 2 is a perspective view of the working end of the resecting device of FIG. 1 showing an asymmetric ceramic housing and moving electrode that is adapted to sweep across a tissue-receiving window.
Figure 3:
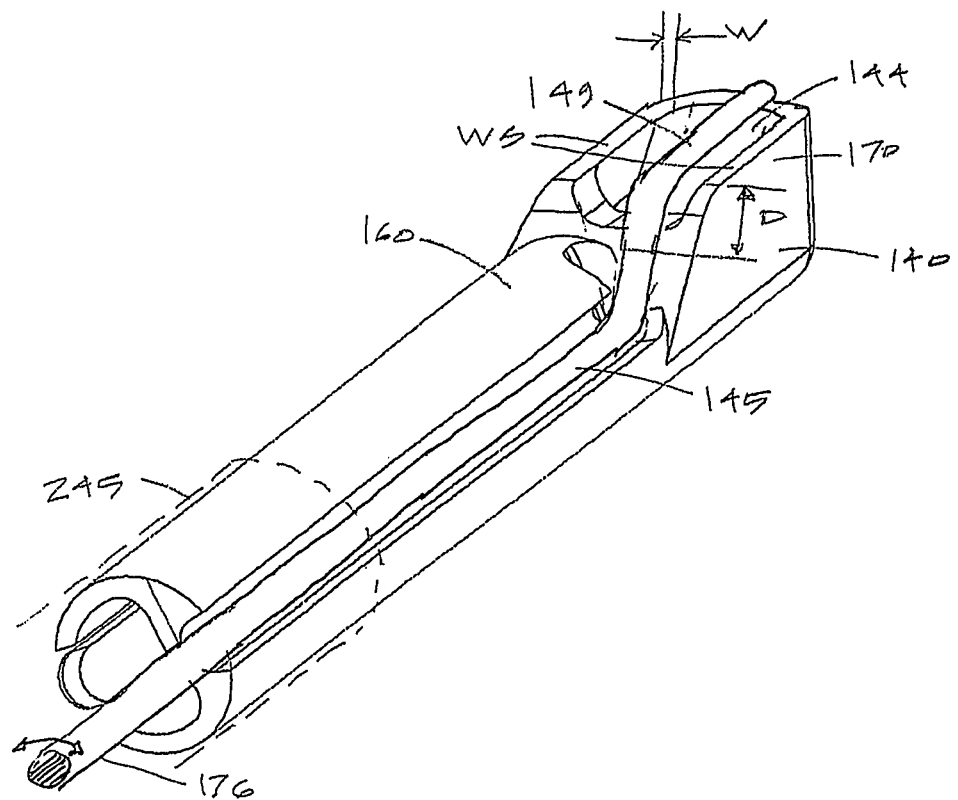
FIG. 3 is another perspective view of the working end of FIG. 2 from a different angle.

Referring to FIGS. 1-3, in general, it can be seen the resecting device 105 has an elongated shaft 110 that extends to a distal shaft portion 132 that is coupled to an offset resecting housing 140 that has an offset tissue-receiving window 144. A moveable electrode 145 is adapted to be driven by a motor drive unit 148 in handle 108 (see FIG. 1) so that the longitudinal portion 149 of the electrode 145 sweeps across the window 144 from side to side to electrosurgically resect tissue that is captured in the window 144. The targeted tissue can be suctioned into and captured in window 144 by means of a negative pressure source or outflow pump 150 in controller 155 that communicates with a tissue extraction channel 158 extending through the device 105 and terminating in the window 144.

Figure 4A:
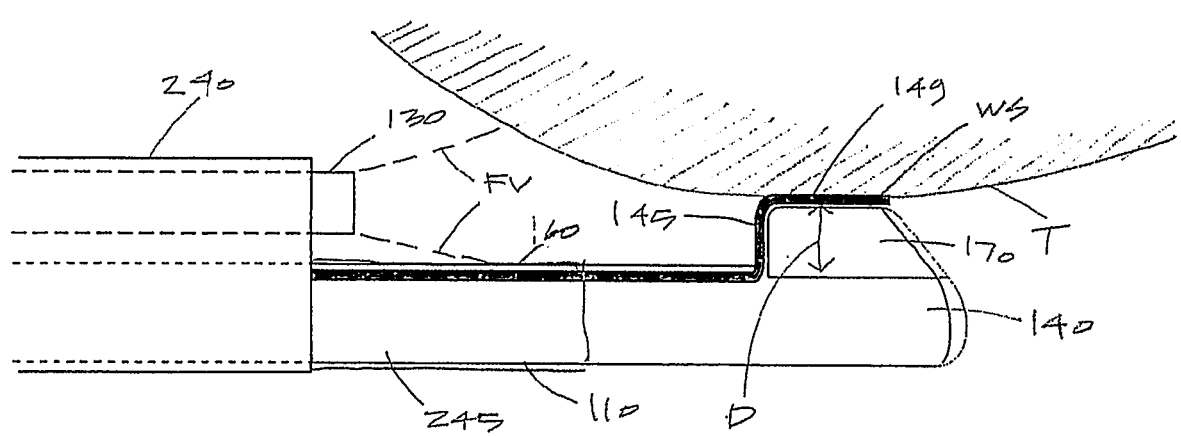
FIG. 4A is a schematic view of the working end of FIGS. 2-3 interfacing with tissue targeted for resection under endoscopic vision.

More in particular, referring to FIGS. 2 and 3, the configuration of the offset housing 140 is adapted to perform multiple functions. First, the offset housing 140 positions the window surface WS (within curved plane P indicated in FIG. 2) outwardly from the outer surface 160 of shaft 110 which then allows the window surface WS to be fully visible through an endoscope 130 or other viewing means that would be introduced parallel to the device shaft 110 (see FIG. 4A). For example, FIG. 4A is a schematic view of the working end 115 with working surface WS in contact with targeted tissue T. As can be seen in FIG. 4A, the endoscope 130 is positioned with the field of view FV directly aligned with the working surface WS thus allowing optimal viewing of the tissue resection process.

Figure 4B:
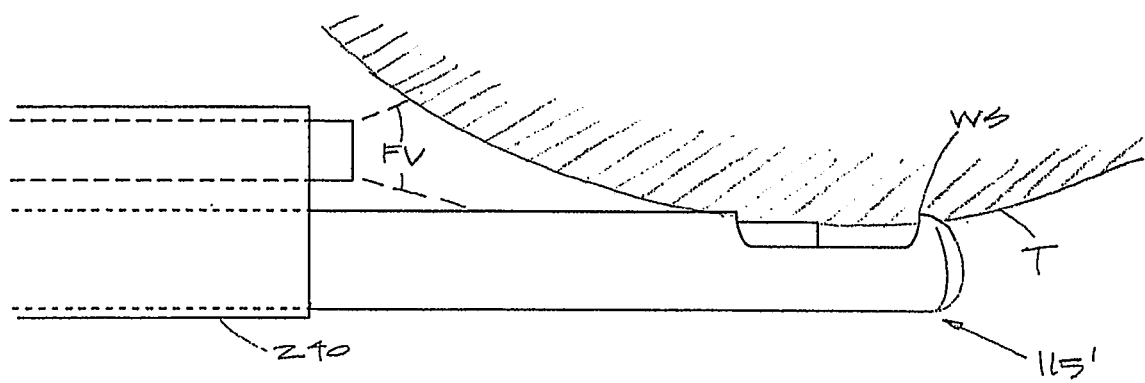
FIG. 4B is a schematic view of a working end of a prior art tubular cutting device used in a hypothetical resection procedure.

In contrast, FIG. 4B shows a working end 115' of a conventional dual sleeve tubular cutter having a window surface WS' which when pressed against an organ prevents endoscopic vision of the interface between the tubular cutting edge and the tissue T during a resection procedure.

Figure 5:
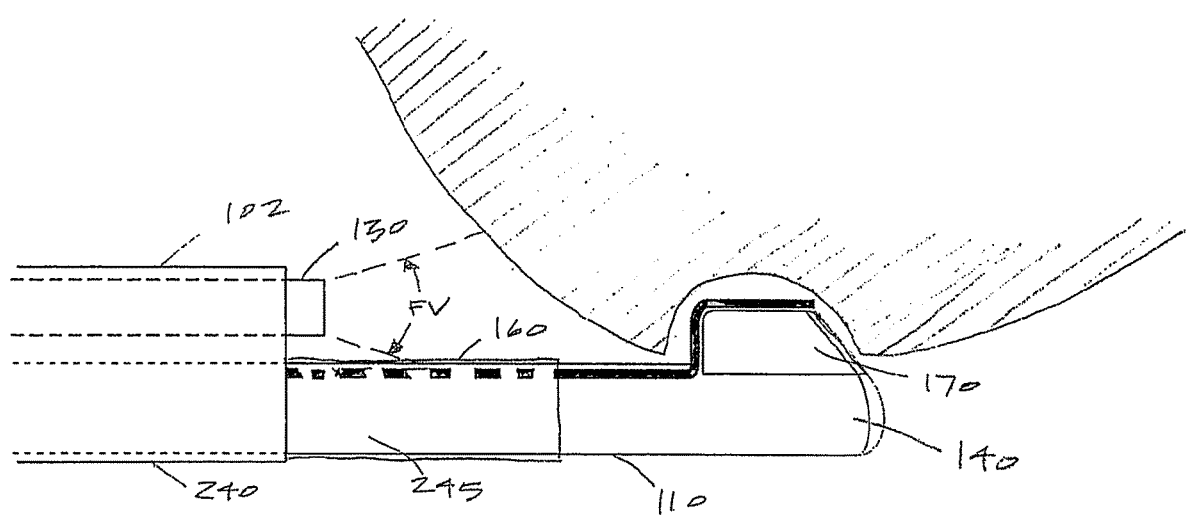
FIG. 5 is another schematic view of the working end of FIGS. 2-3 being used to resect targeted tissue to a significant depth from the organ surface.

Second, the offset housing 140 is adapted for resecting tissue to a greater depth in a localized region of an organ, rather than resecting surface tissues over a broad area. More in particular as shown in FIG. 5, the offset portion 170 of housing 140 can be pushed into tissue perpendicular to axis 112 of the probe shaft 110. Thus, as shown in FIG. 5, the offset housing 140 can be used to resect tissue deep into in a localized region that would not be possible with a resecting device having the configuration shown in FIG. 4B.

FIGS. 2 and 3 illustrate the asymmetric or offset dielectric housing 140 that can comprise a ceramic material such as zirconium oxide, aluminum oxide or similar materials as is known in the art. In FIGS. 2-3, it can be seen that window surface WS is offset from the shaft surface 160 by a predetermined dimension D which can be from 2 mm to 8 mm and in one embodiment comprises a 5 mm offset.

As can be further be seen in FIGS. 2-3, the width W of the window surface WS around at least portions of the perimeter of the window 144 is a limited dimension, for example less than 3 mm, or less than 2 mm or less than 1 mm. which allows the offset portion 170 of housing 140 to be pushed into tissue perpendicular to the device axis 112 as the electrode 145 sweeps across the window 144.

Referring to FIGS. 2-3, one variation of resecting device 105 has an electrode 145 that can be tungsten or stainless steel wire that with electrode portion 149 adapted to sweep across the window 144 at any suitable rate, for example from 1 cycle per second (CPS) to 50 CPS or more. In FIG. 3, it can be understood that the electrode 145 has an elongated proximal shaft portion 176 that extends into handle 108 of the device (FIG. 1). The proximal end of electrode 145 is operatively coupled to a motor drive unit 148 and a suitable mechanism or controller is provided to rotate the elongated electrode shaft portion 176 in an arc to resect tissue.

As can be understood from FIGS. 2-3, the electrode portion 149 moves back and forth akin to a windshield wiper across window 144 in the offset housing 140. A number of mechanisms can be used to effectuate the desired movements of the electrode, or the motor drive 148 simply can be controlled by software to move in intermittent clockwise and counter-clockwise directions. In one variation, the elongated proximal portion 176 of the electrode 145 will twist over its length and thus the motor drive 148 can be adapted to rotate the electrode shaft in an arc with radial angle which is greater than the window's comparable radial angle or arc. Thus, the electrode portion 149 can be expected to move back and forth entirely across the window even when meeting some tissue resistance by compensating for some twisting that is allowed in the proximal electrode shaft portion 176. In one variation, the motor drive unit can be adapted to over-rotate the electrode shaft portion 176 at its proximal end by a selected amount which can be from 10° radial motion to 90° radial motion to compensate for twisting of the electrode shaft portion to insure that electrode portion 149 sweeps entirely across the surface of window 144.

In general, the window 144 in housing 140 can be configured to have a radial arc relative to the electrode shaft 176 ranging between 30° and 180°. In one variation of housing 140' shown in FIG. 6, it can be seen that the electrode portion 149 has a range of motion that extends across the radial dimension of the window 144 to ensure that any tissue captured in the window is resected as the electrode portion 149 passes the window edges 182a and 182b to function like a shear or in a scissor-like manner. The electrode portion 149 moves over ledges 186a and 186b on either side of the housing 140' and can bump into surfaces 190a and 190b. By bumping into the surfaces 190a and 190b, any over rotation in the electrode shaft 176 to accommodate twisting as described above can limit the rotation of the electrode portion in the housing 140'. Further, in FIG. 6, it can be seen that the distal tip 192 of electrode portion 149 extends distally beyond window 144 and onto distal ledge 194 in the housing 140' to ensure tissue is resected by the electrode in the distal window region.

Now turning back to FIG. 1, it can be understood that the resecting device 105 and endoscope 130 can be used with introducer sleeve assembly or sheath 102. As shown in FIG. 1, the introducer assembly 102 has a proximal handle body 202 with a connector 204 that is adapted to couple to connector member 205. The connector 205 is adapted to couple a conduit 206 to controller 155 and provide within a single cable the following: (i) a first lumen communicating with the fluid outflow pump 150, (ii) a second lumen communicating with a fluid inflow pump 225, and (iii) a third lumen communicating with a pressure sensor positioned in the controller 155 or in or near the connector 205. As can be seen in FIG. 1, the introducer sleeve 102 can also accommodate an endoscope 130. Thus, the introducer sleeve 120 can be assembled with the endoscope 130 (and without the resection device 105) and coupled by connector 205 to the controller 155 to provide an inflow of irrigation fluid from fluid source 226, and outflow of irrigation fluid to collection reservoir 228 together with pressure sensing to allow the assembly to be used in a diagnostic procedure prior to a tissue resection procedure. In other words, the introducer sleeve 102 can function as a 'continuous flow' optical introducer for use in trans-urethral access to a targeted sire in the prostate or bladder.

After the introducer sleeve assembly 102 is used for an initial diagnostic procedure, the endoscope 130 can be removed from the assembly 102 and connector 205 can be disconnected from handle body 205. Thereafter, the sleeve portion 240 (see FIG. 1) of introducer assembly 102 can be detached from proximal handle body 204 with the sleeve portion 240 remaining in the patient. Next, the endoscope 130 and connector 205 can be assembled with the resecting device 105 and the physician can insert the resecting device 105 through the sleeve portion 240 remaining in the patient to access the targeted site. The resecting device 105 and sleeve portion 204 in combination then provide lumens as described above for fluid inflows, fluid outflows and direct pressure sensing through lumens in connector 205.

Figure 6:
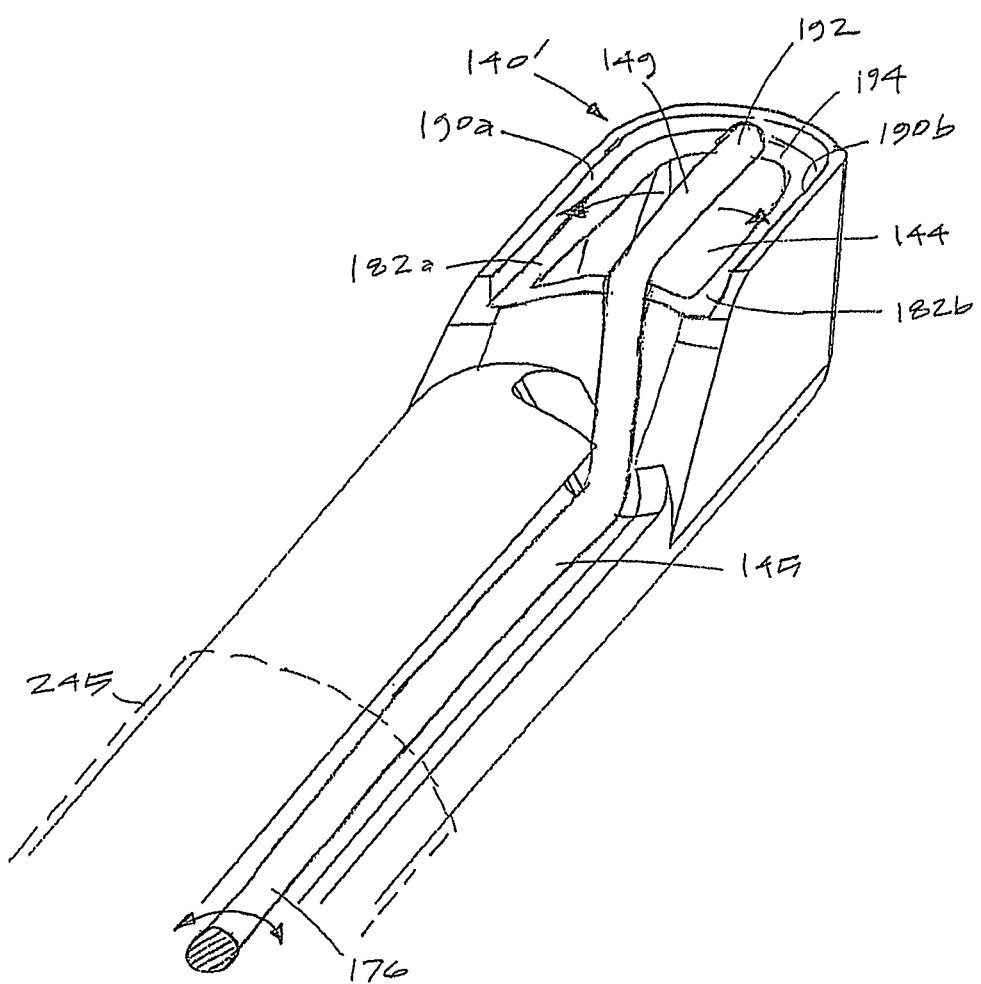
FIG. 6 is a perspective view of a distal dielectric housing of a working end similar to that of FIGS. 2-3 showing window sides with ledges for receiving the electrode at the ends of its movement in a sweeping arc.
Figure 7A:
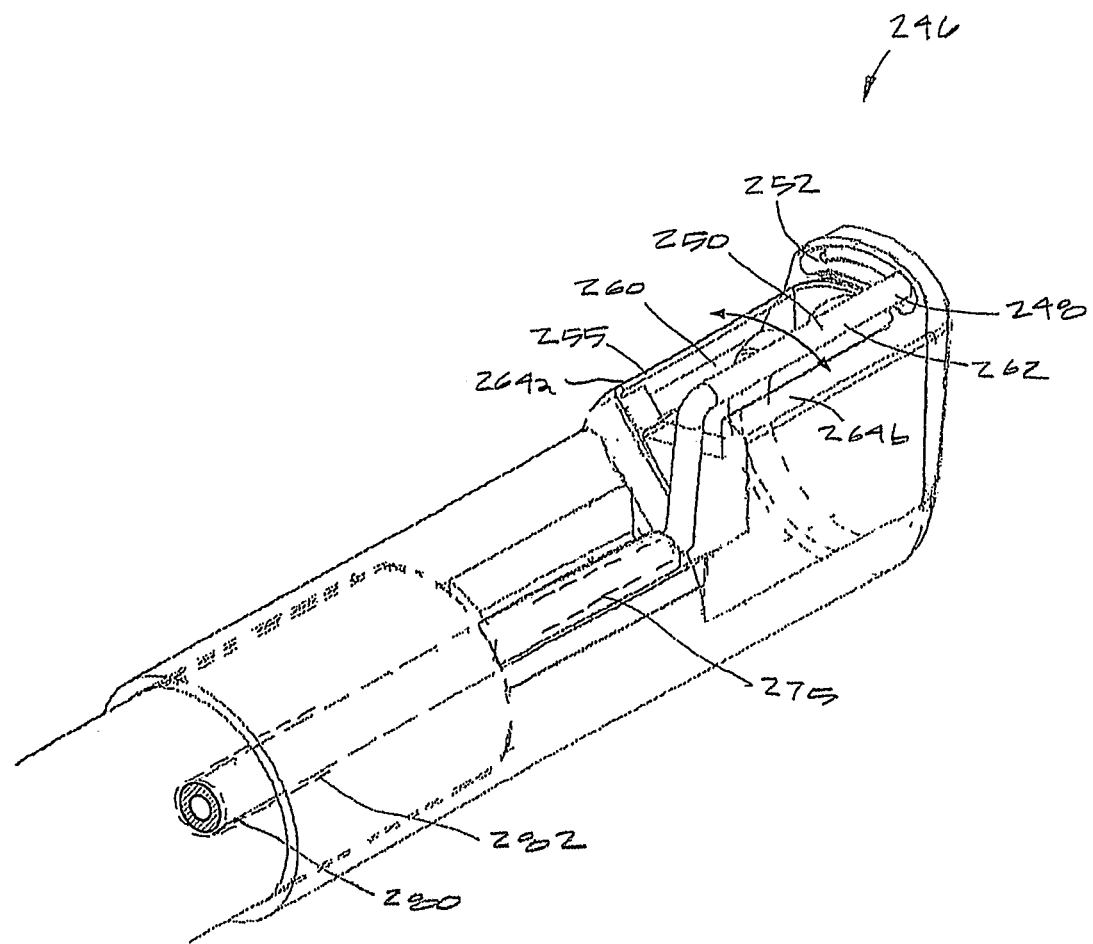
FIG. 7A is a perspective view of a distal ceramic housing of a working end similar to that of FIG. 6 with the distal tip of the moveable electrode adapted to move in a constraining slot or channel.

Now turning to FIG. 7A, a perspective view of a distal ceramic housing of a working end 246 similar to that of FIG. 6 is shown. In this variation, the distal tip 248 of the moveable electrode 250 is configured to be constrained within a constraining slot or channel 252. In other words, the distal electrode tip 248 is not free-floating as in the variation of FIG. 6. It has been found that an electrode with a free-floating distal tip can be caught by tissue and be lifted away from the ceramic housing 255. Thus, in this variation the distal electrode tip 248 is constrained and cannot be tangled with tissue or lifted away from the ceramic housing and window 260. The variation of FIG. 7A illustrates an arcuate slot or channel 252 that limits the movement of the electrode 250. In all other respects, the working end functions as described previously. Further, the distal electrode portion 262 and channel 252 can be configured to allow the electrode to pass over the edges 264a and 264b of the window 260 as described above.

Figure 7B:
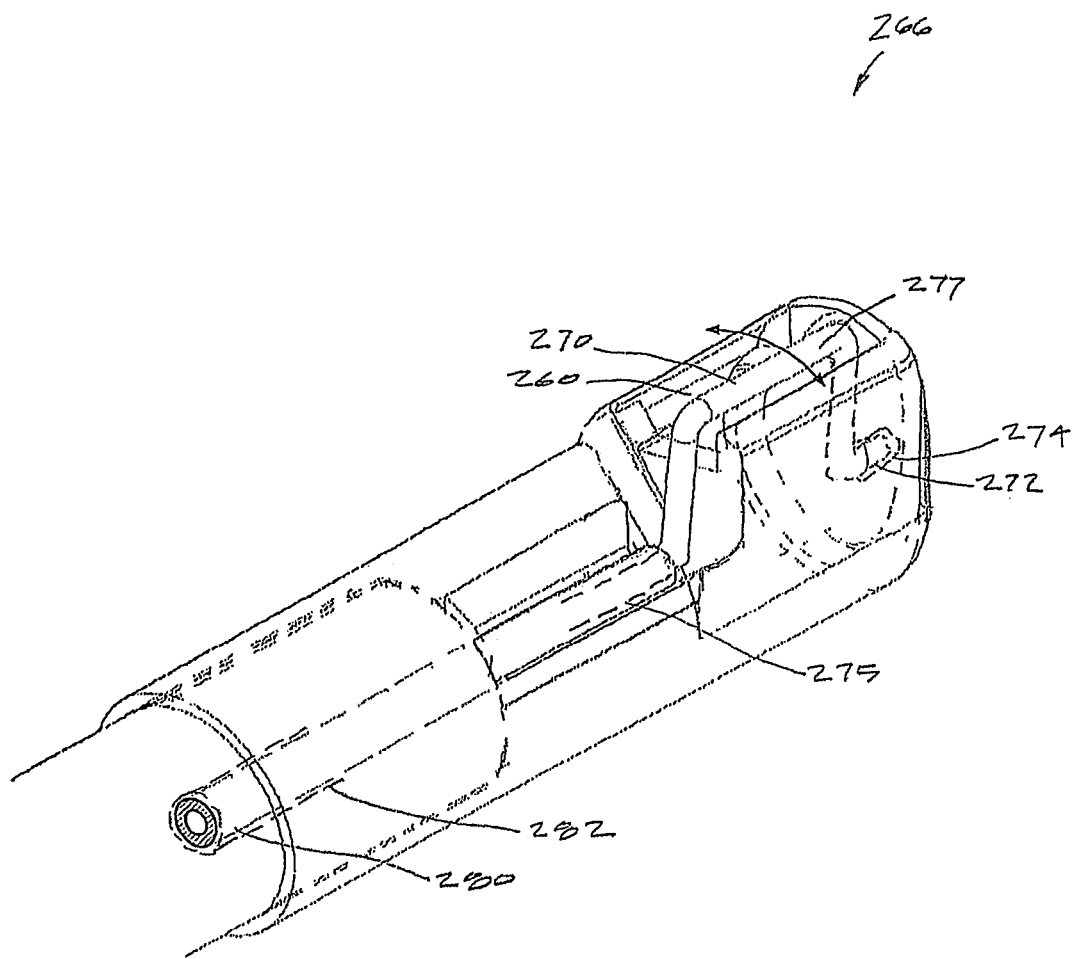
FIG. 7B is a perspective view of an alternative ceramic housing similar to that of FIG. 7A with the distal tip of the moveable electrode adapted to pivot or rotate in a bore or pivot.

FIG. 7B shows another variation of working end 266 in which the electrode 270 has a distal tip 272 that is constrained in a pivot or bore indicated at 274. In this variation, it can be seen that the electrode 270 has a U-shape with the distal tip 272 aligned with the electrode shaft portion 275 to allow the active electrode portion 277 to move from side to side relative to window 260 as described previously.

In another aspect of the invention shown in FIGS. 7A-7B, the electrode shaft portion 275 comprises a tubular member 280 which can comprise a metal hypotube, such as stainless steel or a similar material. In a previous variation as shown in FIG. 6, the electrode shaft portion comprised a wire element which could potentially twist to an unwanted degree when the electrode engaged dense tissue, for example. In this variation, it has been found that a metal hypotube with a suitable wall thickness can resist twisting when the electrode is being moved and engaging dense tissue. In one variation, the wall thickness of the tubular member 280 can be at these 0.005" or at least 0.010".

In general, a tissue resecting device corresponding to the invention comprises an elongated member extending along a longitudinal axis to a distal portion having a window communicating with an aspiration source, an electrode having an electrode shaft with a central axis extending within the elongated member to an electrode working end wherein a portion of the electrode working end is offset from said central axis, and a motor configured to rotate the electrode shaft to cause the electrode working end to move relative to the window wherein the electrode shaft comprises a tubular member adapted to resist twisting of said shaft during motor driven movement thereof. Further, the tubular member can comprise a metal tube with an insulative outer surface layer 282. The tissue tubular member can be a stainless steel tube with the insulative outer surface layer comprising a heat shrink polymer.

In one variation, the electrode's working end has a profile that is substantially smaller than the area of the window to thereby permit fluid aspiration around the electrode working end at all times through the window as the electrode is moving relative to the window. This allows the negative pressure source to draw the tissue into the window interface, and maintains the tissue in the interface as the electrode cuts and extracts the resected tissue. In one variation, the electrode working end is motor driven and moves at a rate of equal to or greater than 1 CPS relative to the window, or equal to or greater than 10 CPS relative to the window. As described previously, the electrode working end can be offset radially outward from the shaft assembly by at least 2 mm or by at least 4 mm.

In another aspect of the invention, the tissue resecting device comprises an elongated member extending to a distal housing having a tissue-receiving window, a moveable electrode configured to move across the window, and a motor configured to move the electrode wherein a distal tip of the electrode moves in a constraining channel in the housing. In another variation, the tissue resecting device comprises an elongated member extending to a distal housing having a tissue-receiving window, a moveable electrode configured to move across the window; and a motor configured to move the electrode wherein a distal end of the electrode is non-free floating or pivots in a pivot channel.

Figure 8:
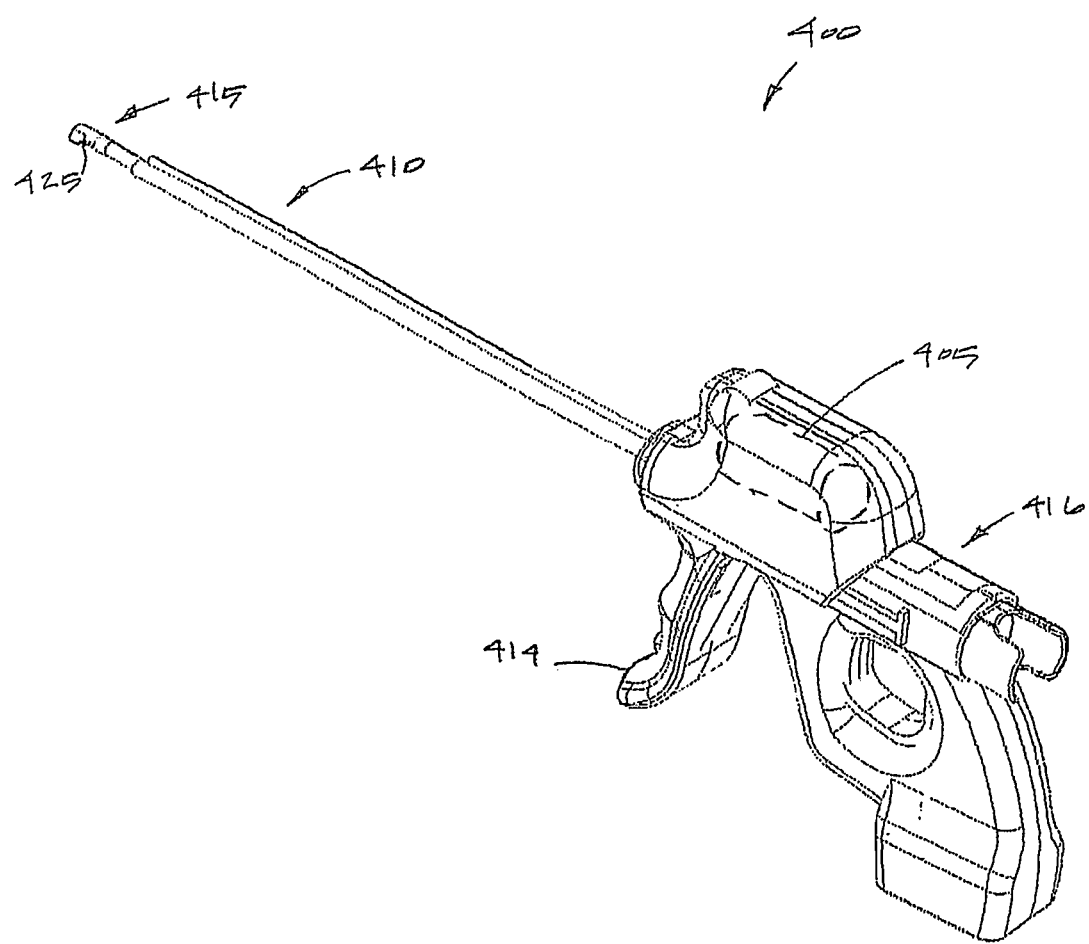
FIG. 8 is a perspective view of a tissue resecting device that includes a motor drive for moving the shaft assembly and working end in a reciprocating mode relative to the handle.

FIG. 8 is a perspective view of a tissue resecting device 400 that includes a handle 402 carrying a motor drive 405 and a shaft assembly 410 extending from the handle to a working end 415, for example comprising a ceramic or other housing 418 (FIGS. 9A and 9B) having a tissue-receiving window 420 and a motor-driven electrode 425 that is adapted to move across the window 420 as described previously. The working end 415 is coupled to sleeve 428 which is adapted for manual or motor-driven reciprocation within shaft assembly 410. More in particular, this variation of device 400 provides the motor drive 405 for moving the electrode 425 in the working end 415 which is similar to that of FIG. 7A. Further, in this embodiment, the device 400 can optionally utilize the motor drive to reciprocate the working end 415 relative to the shaft assembly 410 contemporaneously or alternatingly with the movement of the electrode 425 relative to the window 420 as described previously. Alternatively, the device 400 carries a first motor for moving the electrode 425 relative to the window 420 in the housing 418 and a second motor (not illustrated) for reciprocating the working end 415. In another variation, the single motor 405 can be adapted to perform both the electrode movement and the working end reciprocation. As can be seen in FIGS. 10A-10B, the handle 402 allows for manual retraction and extension of the working end 415 within the shaft assembly 410 by movement of an actuator grip 430 relative to stationary grip portion 432 of handle 402.

Figure 9A:
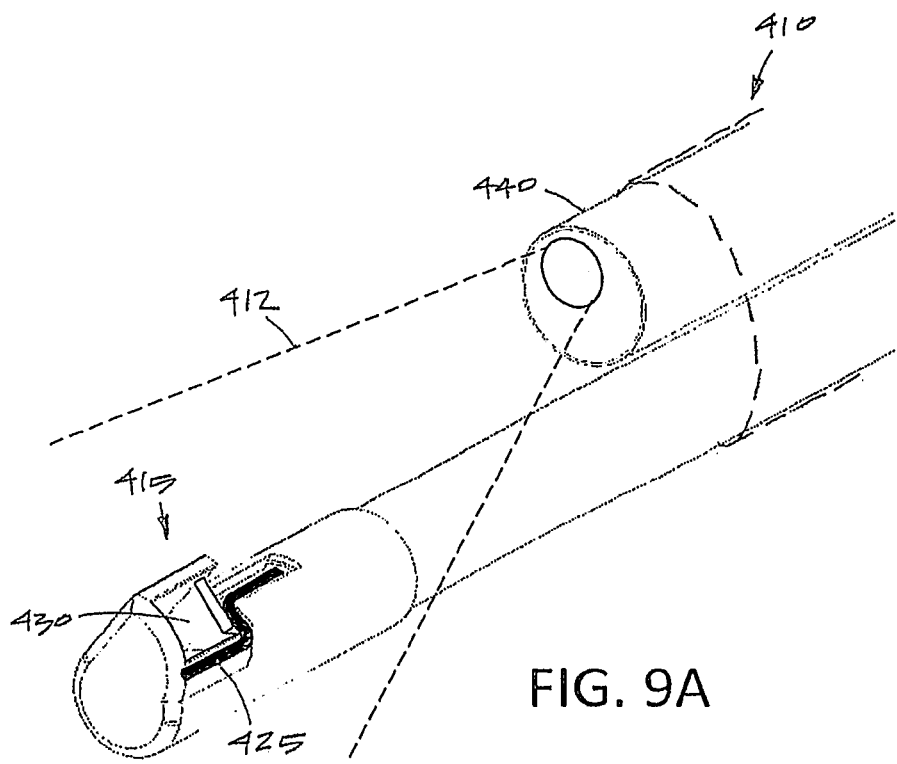
FIG. 9A is a perspective view of the working end of the device of FIG. 8 showing an endoscope carried by the shaft assembly and the endoscope field of view.
Figure 9B:
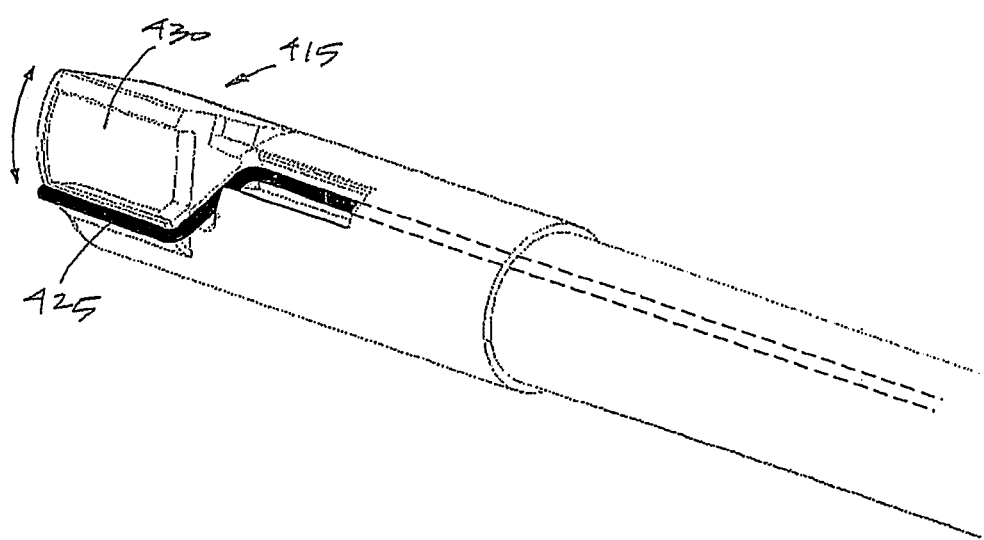
FIG. 9B is a perspective view of the working end of the device of FIG. 9A from another angle.
Figure 10A:
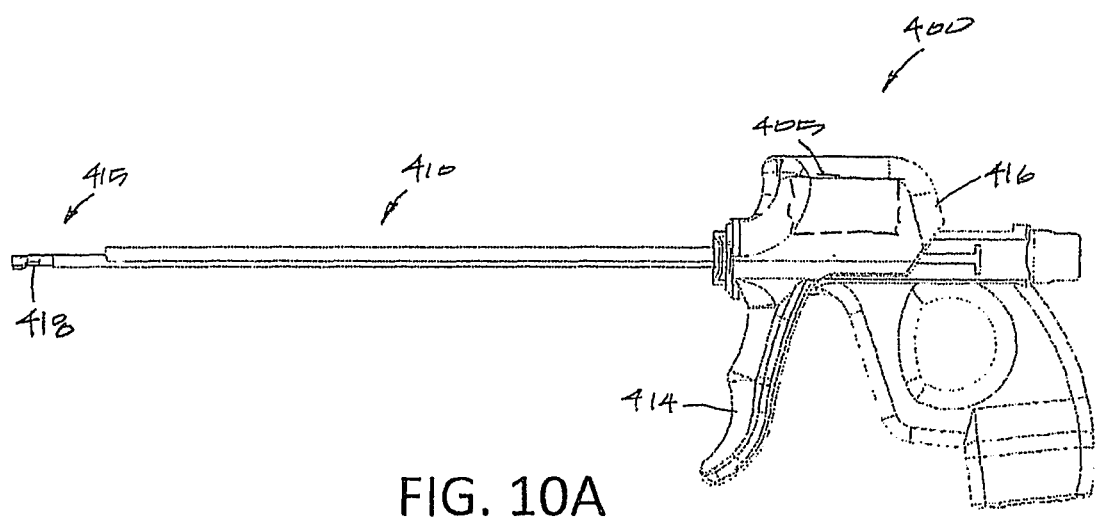
FIG. 10A is a side view of the tissue resecting device of FIG. 8 with the reciprocating shaft assembly and working end at the distal end of an extending stroke relative to the handle.
Figure 10B:
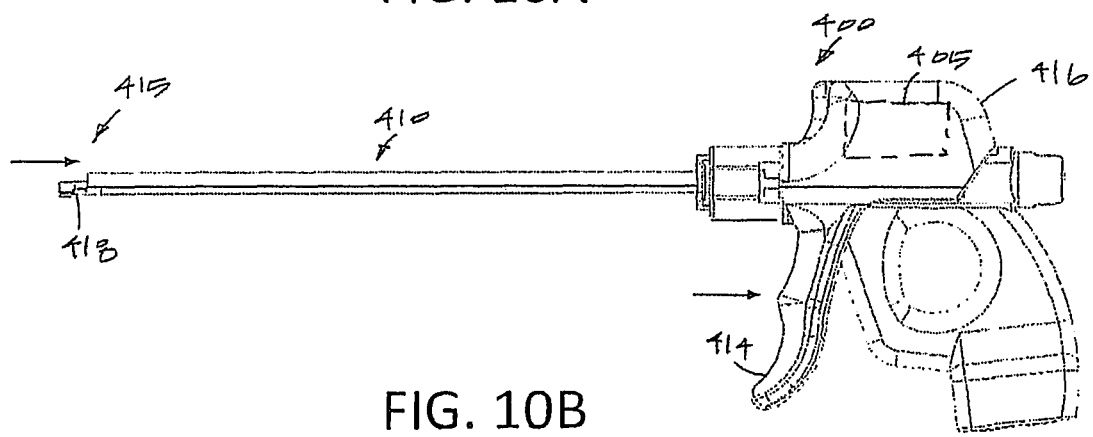
FIG. 10B is a side view of the tissue resecting device of FIG. 10A with the reciprocating shaft assembly and working end at the proximal end of a retracting stroke relative to the handle.

FIG. 9A is a perspective view of the working end 415 of the device 400 of FIG. 8 showing an endoscope 440 carried with an outer sleeve 442 of the shaft assembly 410. The working end 415 carried by sleeve 428 is similar to that of FIGS. 2, 3, and 6 described previously, but could have any of the constructions described previously. The endoscope 440 has optics 444 which provide a field of view 445 which can encompass the working end 415 on the elongated member 428. A light emitter 446 is shown in the distal end of the endoscope 440. FIG. 9B is a perspective view of the working end of the device of FIG. 9A from another angle.

FIGS. 10A and 10B are side views of the tissue resecting device 400 of FIG. 8 illustrating reciprocation of the sleeve 428 and working end 415 within shaft assembly 410 and relative the stationary grip portion 432 of handle 402. FIG. 10A shows the sleeve 428 and working end 415 at a distal end of an extending stroke relative to the shaft assembly 410 and handle 402, and FIG. 10B shows at the working end 415 and sleeve 428 at a proximal end of a retracting stroke relative to the handle. In this variation, the working end 415 and sleeve 428 are adapted to reciprocate while the endoscope 440 remains stationary in the handle 402. In alternative embodiments (not shown), the working end 415 and sleeve 428 may be configured to axially reciprocate together with the endoscope 440 in the shaft assembly 410.

Figure 11:
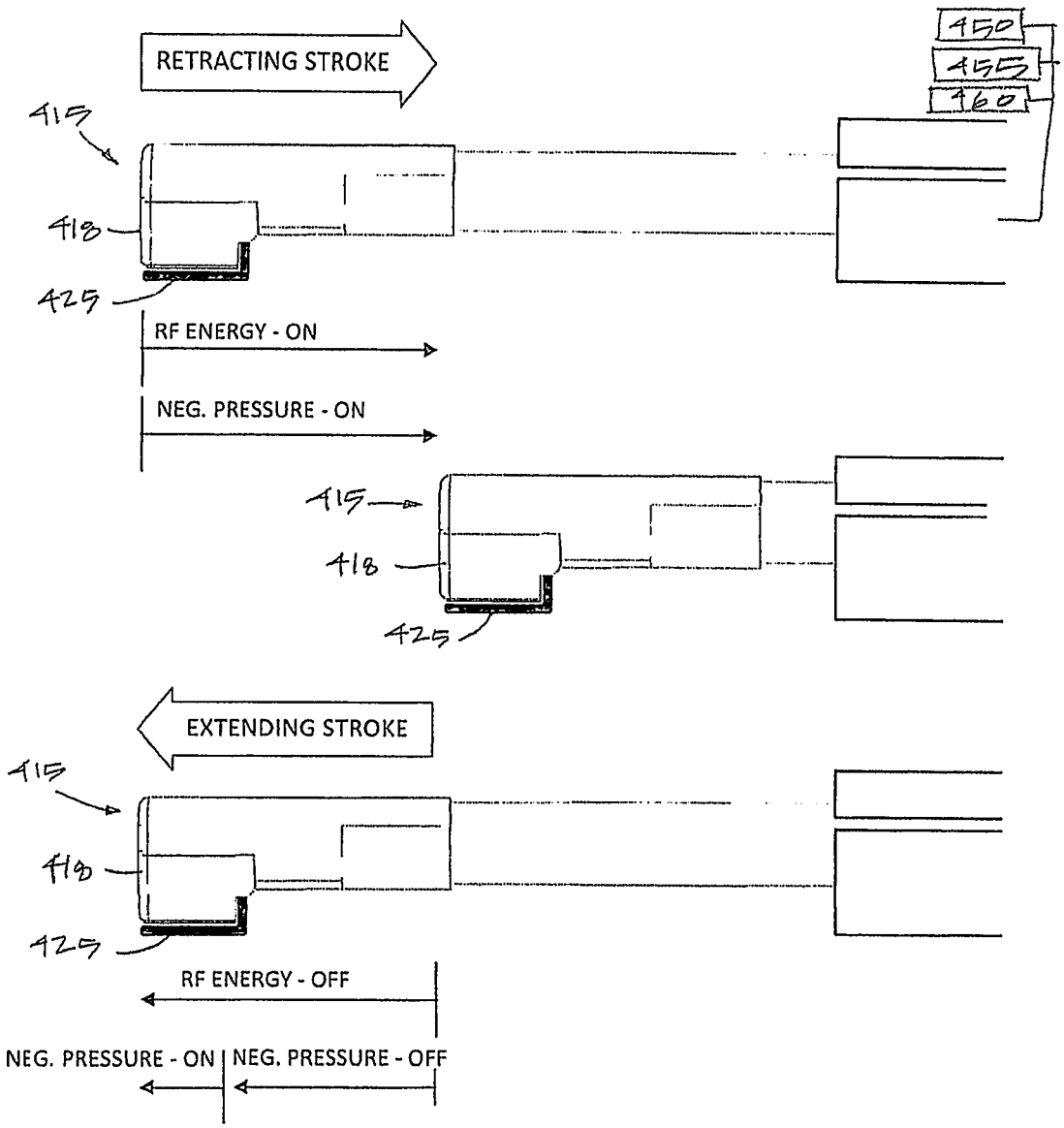
FIG. 11 is a sequential view of the tissue resecting device of FIGS. 10A-10B showing retracting and extending strokes and a method of activating and de-activating the negative pressure source and the delivery of RF current to the electrode in different portions of the retracting and extending strokes.

FIG. 11 illustrates a method according to the invention showing retracting and extending strokes of the working end 415 and sleeve 428 wherein a controller 450 activates and de-activates a negative pressure source 455 and causes delivery of RF current from an RF source 460 to the moveable electrode 425 in different portions of the retracting and extending strokes.

The methods of the present invention can employ any tissue resecting device having a moveable working end such as working end 415 and moveable sleeve 428 described previously, extending along a longitudinal axis to a distal housing 418 and having a window, such as window 420 in communication with a remote negative pressure source 455, a moveable electrode 425 configured to move relative to the window 420 and at least one motor 405 adapted to move the electrode across the window 420 and optionally to reciprocate or otherwise move the working end 415 in an axial stroke. The motor drive 405 can be adapted to rotationally oscillate the electrode at any of the rates set forth previously herein, often being greater than 1 CPS (cycles per second) relative to the window. Optionally, the motor can be used to axially reciprocate the sleeve 428 and working end 415 at least once every 2 seconds or at least once per second relative to the handle.

In another variation, the tissue resecting device is coupled to a controller 450 that is configured to operate (1) the RF source 460 coupled to the electrode, (2) the negative pressure source 455, and (3) the at least one motor 405 for moving the electrode 425 and optionally for reciprocating the working end 415 within the shaft assembly 410. Further, the controller may be adapted to control the at least one motor drive to stop movement of the electrode 425 in a selected position relative to the window 420. More in particular, the controller can be adapted to selectively stop the electrode 425 in the center of the window 420 or at an edge of the window.

In still further variations, the controller 450 is adapted to control the at least one motor drive 405 to provide a single movement or cycle of the electrode 425 back and forth across the window 420. In yet another variation, the controller 450 is adapted to control the at least one motor to stop movement of the working end 415 and sleeve 428 in a selected axial position relative to the shaft assembly 410.

Referring again to FIG. 11, the controller 450 can be adapted to control the at least one motor drive 405 to provide a single movement of the shaft assembly in a retracting and extending stroke. In another embodiment, the controller 450 is configured to operate the RF source 460, the negative pressure source 455 and the at least one motor drive 405 contemporaneously. For example, the controller 450 can be adapted to modulate the negative pressure source 455 in response to movement of the working end, or activate or de-activate the RF source in response to movement of the working end, or modulate the negative pressure source in response to movement of the electrode 425 relative to the window, or activate or de-activate the RF source in response to movement of the electrode 425 relative to the window 420 in ceramic body 418. Further, the RF source 460 can be configured to deliver a cutting current waveform or a coagulation waveform to the electrode.

Referring to FIG. 11, a method of resecting tissue according to the present invention comprises providing an elongate shaft assembly, such as assembly 410, having a longitudinal axis and including a reciprocating sleeve 428 carrying a working end 415 comprising a distal housing 418 having an electrode 425 proximate a window 420 in the housing. The sleeve 428 and working end 415 are moveable relative to a stationary portion of the handle 402 with a retracting stroke and an extending stroke. The working end 415 is positioned against a targeted tissue site, and a negative pressure source communicating with the window 420 in the working end 415 is activated. An RF source is activated to deliver RF current to the electrode 425 as the motor drive moves the electrode across the window, and the working end 415 is moved in a retracting stroke to thereby resect tissue while the negative pressure source remains activated to draw tissue into contact with the window 420. The method may further comprise de-activating the negative pressure source, the motor drive and typically also the RF source at the proximal end of the retracting stroke, typically via the controller. Subsequently, the method may comprise commencing the extending stroke with the negative pressure source de-activated and with the RF source de-activated. As can be seen in FIG. 11, the controller activates the negative pressure source during a terminal portion of the extending stroke to again draw tissue into contact with the window 420 to prepare for the following retracting stroke which then again resects tissue with the energized, oscillating electrode 425.

As can be understood from the steps of the method described above, variations of the timing of activation and de-activation of the negative pressure source and RF current delivery are possible. In another variation, the electrode can be energized and oscillated to resect tissue in both the retracting stroke and the extending stroke with the negative pressure source continuously activated.

In another variation, the electrode can be stopped in a selected position in the window, and a coagulation current can be delivered to the electrode for coagulating tissue. Alternatively, the cutting current waveform can be delivered to the stationary electrode for ablating tissue.

Figure 12A:
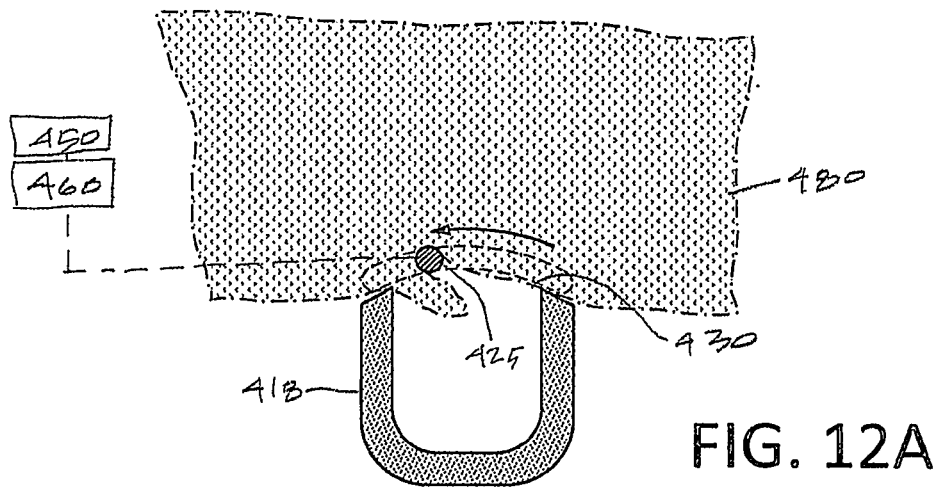
FIG. 12A is a sectional schematic view of the working end with the moving electrode resecting tissue.
Figure 12B:
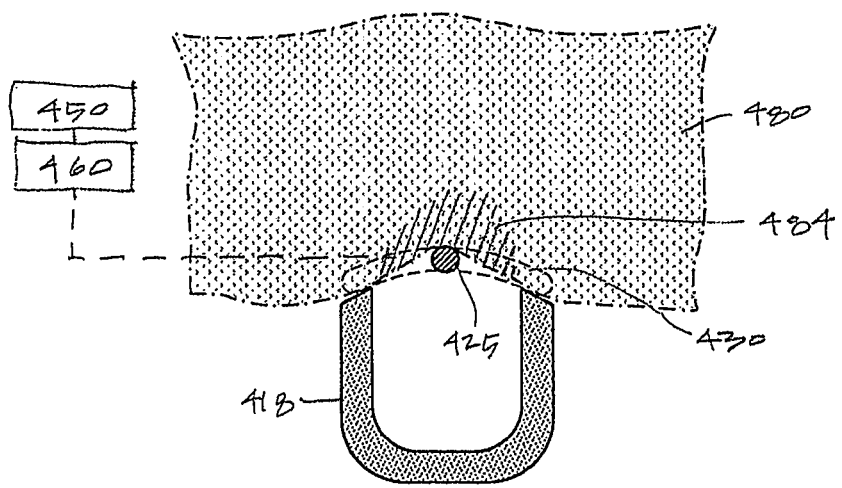
FIG. 12B is a sectional schematic view of the working end similar to that of FIG. 12A with a stationary electrode coagulating tissue.

FIGS. 12A-12B illustrate another aspect of the present invention wherein the controller 450 and RF source 460 can be adapted to deliver an RF current with a cutting waveform to the electrode 425 or an RF current with a coagulation waveform to the electrode in various modes of electrode movement or when the electrode is stationary relative to the window. FIGS. 12A-12B are sectional views of the working end of FIG. 9A or FIG. 11 interfacing or engaging with tissue 480.

In general, a method of treating prostate tissue comprises providing a treatment device with a shaft extending along a longitudinal axis to a distal portion having a window 420 in ceramic body 418 communicating with a negative pressure source and a motor driven electrode 425 adapted to move relative to the window, positioning the window in an interface with targeted tissue 480, operating in a first mode with a cutting waveform delivered to the electrode while activating the motor to move the electrode to resect tissue 480 (FIG. 12A) and thereafter operating in a second mode with a coagulation waveform delivered to the electrode 425 after de-activating the motor to stop the electrode 425 in a selected stationary position to coagulate tissue indicated at 484 (FIG. 12B). Further, the positioning step can be preceded by the step of introducing the shaft in a trans-urethral approach into a patient's prostate. The first mode includes sweeping the electrode 425 across the window 420 to resect tissue interfacing the window as shown in FIG. 12A. The electrode 425 can be adapted to sweep across the window from side to side, or in another variation can move distally and proximally in the window 430.

In the first mode, the electrode 425 can move at a rate of greater than 1 CPS relative to the window 430. Further, operating in the first mode includes activating the aspiration source within a first negative pressure range to draw tissue against or into the window and to aspirate fluid and resected tissue through the window. Operating in the second mode includes activating the aspiration source within a second negative pressure range to aspirate fluid through the channel in the shaft. When operating in the first and second modes, a controller is utilized to activate and de-activate the motor, the RF source and the negative pressure source in a selected manner.

In another method, the controller can operate the motor and RF source in a third mode to delivering a coagulation waveform while activating the motor to move the electrode at less than 100 CPS.

In another method, the controller can operate the motor and RF source in a fourth mode delivering a cutting waveform after de-activating the motor to stop the electrode in a selected stationary position.

When the device is operated in a mode with a stationary electrode, the selected stationary position of the electrode is substantially centered in the window. Such a centered position allows for aspiration of fluid around both sides of the electrode through the window which cools the electrode in the coagulation mode and remove bubbles when the cutting current is used to ablated tissue.

In general, a tissue resecting device comprises an elongated shaft extending along a longitudinal axis to a distal portion having a window communicating with an aspiration source, a wire-like electrode configured to move relative to the window, an RF source configured to deliver RF current in a cutting waveform and a coagulation waveform to the electrode, a motor configured to move the electrode, and a controller configured to operate the motor and RF source in a first mode delivering a cutting waveform while activating the motor to move the electrode, and in a second mode delivering a coagulation waveform after de-activating the motor to stop the electrode in a selected stationary position. In this variation, the electrode has a surface area smaller than the window area to permit fluid aspiration around the electrode and through the window in the first and second operating modes.

When operating in the first mode, the controller can activate the aspiration source within a first negative pressure range. When operating in the second mode, the controller can activate the aspiration source within a second negative pressure range.

When operating in a third mode, the controller can be configured to operate the motor drive and RF source to deliver a coagulation waveform while activating the motor to move the electrode at less than 50 CPS.

When operating in a fourth mode, the controller can be configured to operate the motor and RF source to deliver a cutting waveform after de-activating the motor to stop the electrode in a selected stationary position, for example in the center of the window.

As can be seen in FIGS. 9A, 9B and 11, the distal portion of the sleeve 428 includes a dielectric body or housing 418 having the window 420 therein. Typically, the housing is a ceramic material which can be selected from the group consisting of yttria-stabilized zirconia, magnesia-stabilized zirconia, ceria-stabilized zirconia, zirconia toughened alumina and silicon nitride. In other variations, the dielectric body can be a polymeric material.

The motor drives shown in FIGS. 8, 10A and 10B can be disposable or detachable and thus re-usable.

As can be understood from the steps of the method described above, variations of the timing of activation and de-activation of the negative pressure source and RF current delivery are possible. In another variation, the electrode can be energized to resect tissue in both the retracting stroke and the extending stroke with the negative pressure source continuously activated.

In another variation, the electrode can be stopped in a selected position in the window, and a coagulation current can be delivered to the electrode for coagulating tissue. Alternatively, the cutting current waveform can be delivered to the stationary electrode for ablating tissue.

Figure 13:
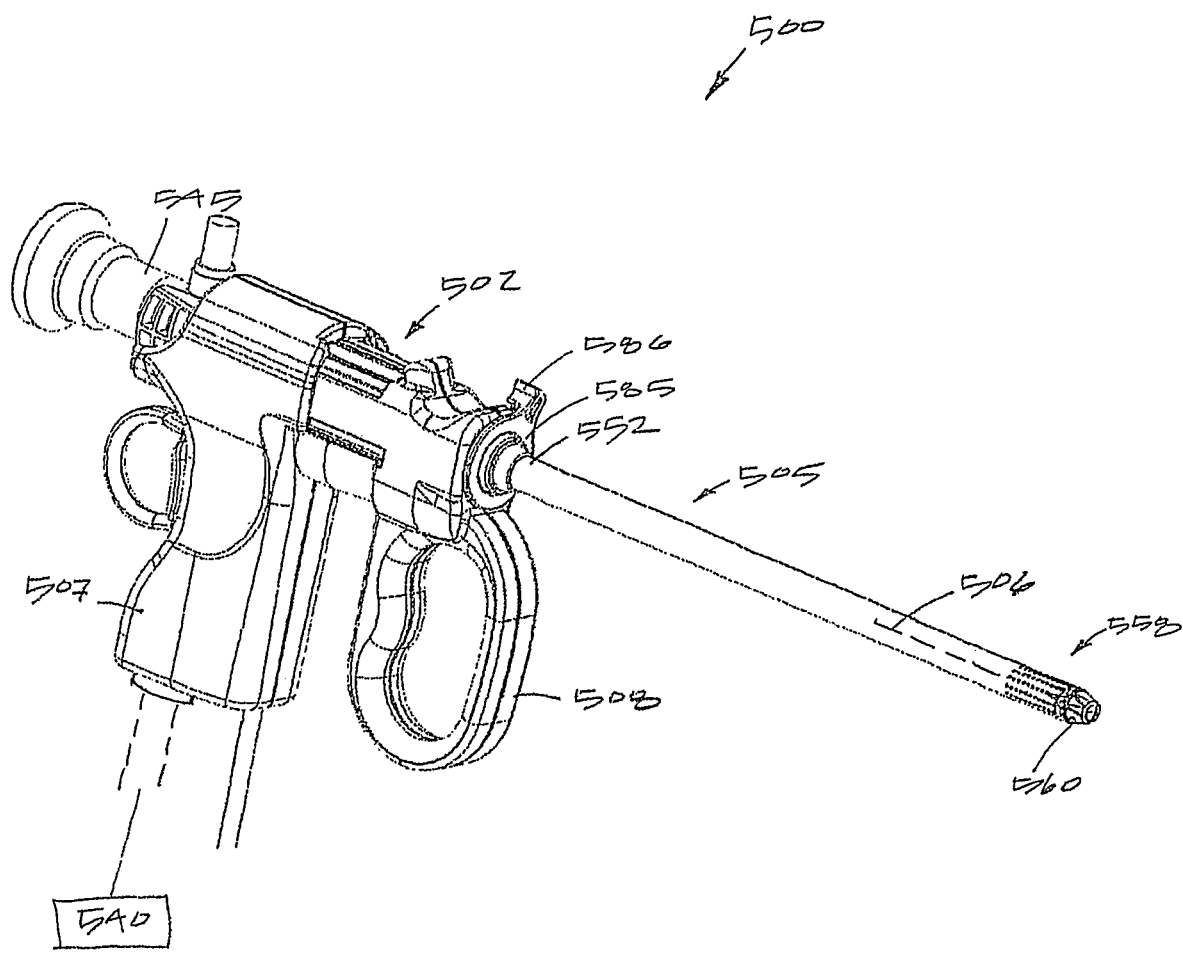
FIG. 13 is a perspective view of another variation of a resecting device of similar to that of FIG. 1 with an integrated introducer sleeve assembly.

FIG. 13 illustrates an alternative embodiment of a resection device 500 that is similar to that of FIGS. 1-2 except that an outer introducer sheath or sleeve is integrated into the resection device and is not a separate component as in the variation of FIGS. 1-2.

Figure 15:
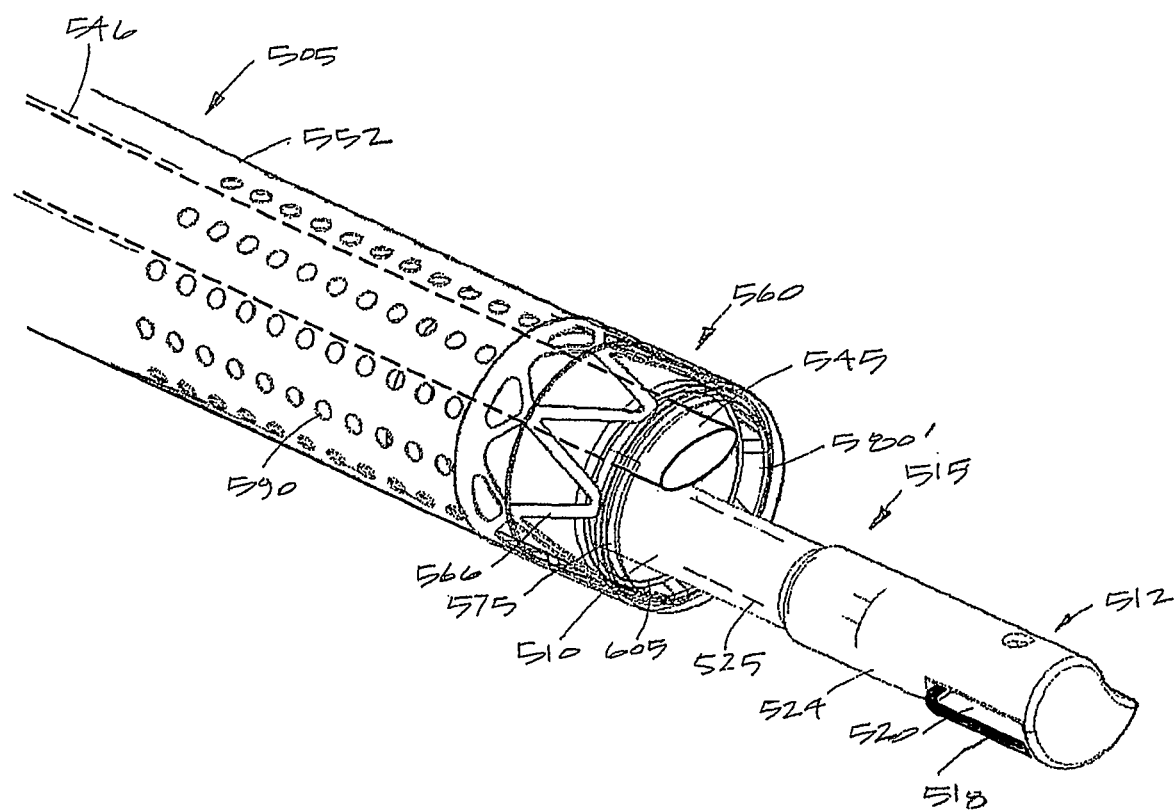
FIG. 15 is a view of the distal end portion of FIG. 14B in its expanded cylindrical shape with a resecting component extending distally beyond the resilient structure.

As can be seen in FIG. 13, the resection device 500 again has a handle 502 coupled to an elongated shaft assembly 505 extending about a longitudinal axis 506. The handle 502 has a stationary grip portion 507 and a movable grip 508 that is adapted to reciprocate a shaft 510 and working end 512 of the resection component 515 (see FIG. 15) which is the same as in previous embodiments. Again, the working end 512 of the resection component 515 includes an RF electrode is 518 that adapted to sweep across an open window 520 in a dielectric housing 524 which can be a ceramic or a polymeric material (FIG. 15). An aspiration channel 525 is provided in the shaft 510 and working end 512 of the resection component 515 to remove tissue chips from the working end 512. A negative pressure source 540 again is coupled to the handle 502 as in previous embodiments for extracting tissue through the aspiration channel 525 of the resection component (FIG. 13). As will be described below, the negative pressure source 540 also communicates with a separate flow pathway 592 in the shaft assembly 505 (see FIG. 17).

Figure 14A:
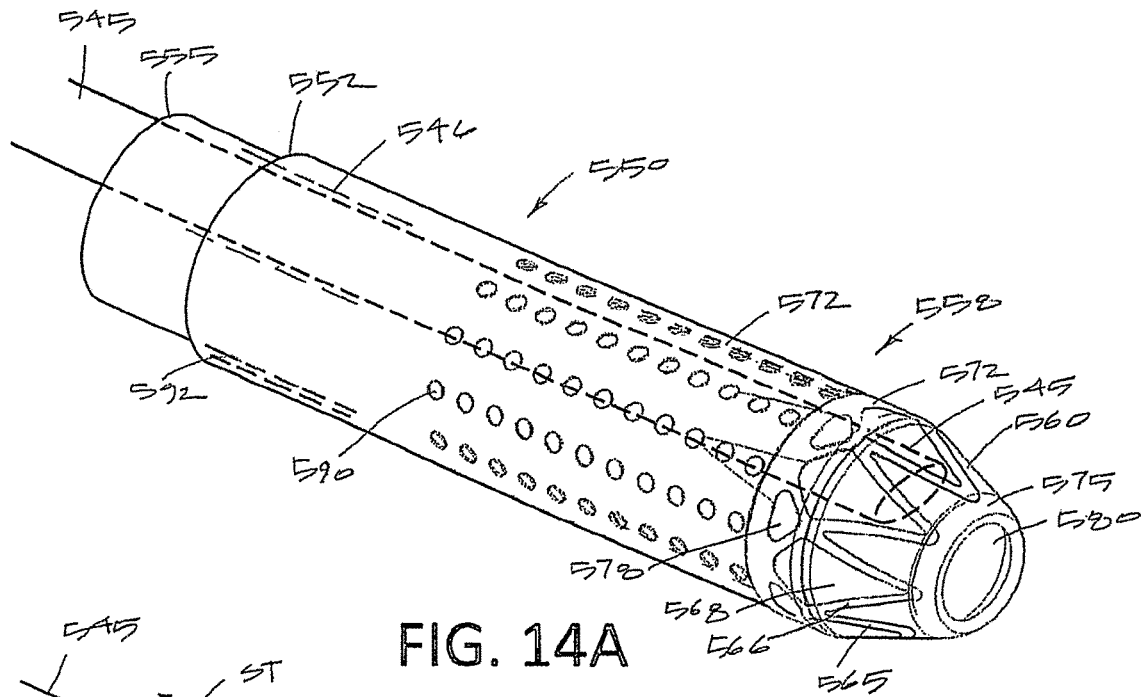
FIG. 14A is an enlarged view of the distal end portion of the resecting device of FIG. 13 showing an expandable, resilient structure in a tapered shape for introduction into a patient's body.

An endoscope 545 is adapted to be inserted into an endoscope channel 546 in the device 500 (see FIG. 14A). In the embodiment shown in FIG. 13, a dedicated pressure sensing channel 548 is also provided in the elongated shaft 505 as in previous embodiments (see FIG. 16).

As can be understood in FIGS. 14A-14B, the resection device 500 has an integrated introducer sleeve assembly 550, whereas the previous versions have an independent introducer sleeve component (see FIGS. 1-2) In FIG. 14A, the introducer sleeve assembly 550 comprises an outer introducer sleeve or tubular member 552 and an inner sleeve 555 described further below. FIG. 13 shows the outer sleeve 552 fixed to the handle 502 which extends to a distal end 558 which comprises a resilient structure 560 that is movable or deformable between a first tapered, rounded-nose shape or similar configuration (FIG. 14A) for introduction through a body passageway and a second cylindrical shape or configuration (FIG. 14B) that allows for the endoscope 545 and resection component 515 device to be advanced into or through the sleeve assembly 550 and resilient structure 560. The outer introducer sleeve 552 can be a thin-wall stainless steel material with a diameter ranging from about 6 mm to 15 mm.

In FIG. 14A, which is an enlarged view of the resilient structure 560 is its tapered position, it can be understood that the structure 560 is in a repose, or non-tensioned and contracted configuration. FIG. 14B show the distal end 558 of the sleeve assembly and resilient structure 560 in a tensioned and expanded configuration.

Figure 14B:
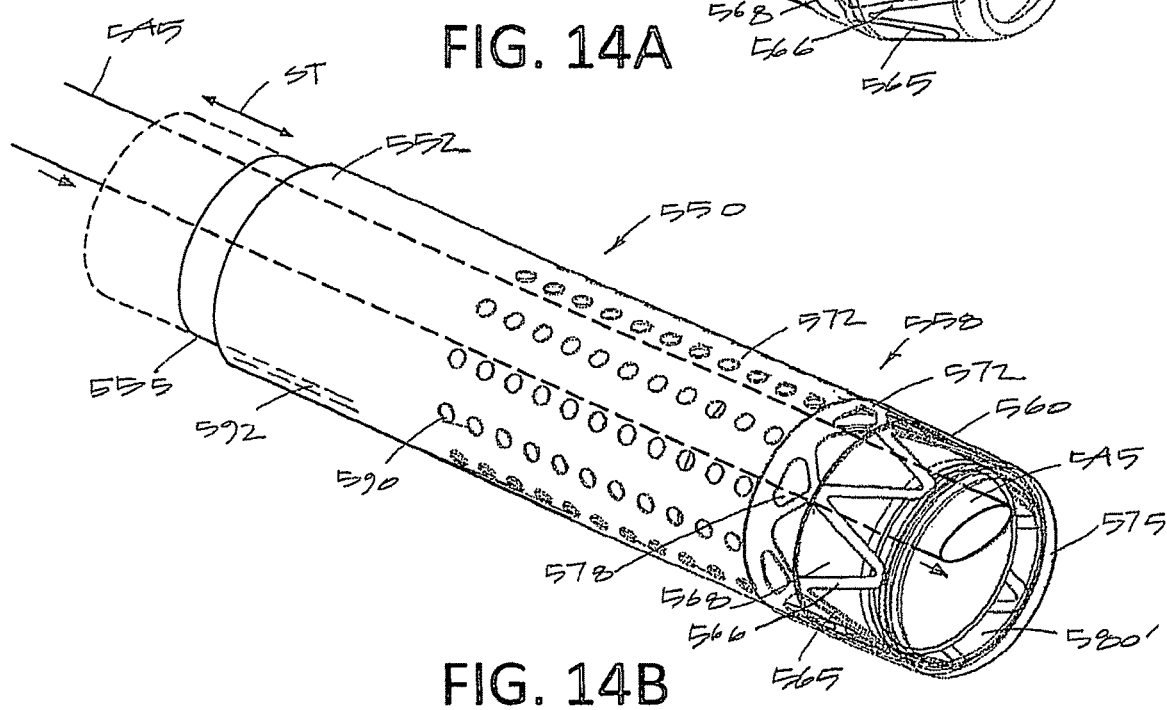
FIG. 14B is another view of the distal end portion of the resecting device of FIG. 14A showing the resilient structure in a second, expanded cylindrical shape for introduction of a resecting component therethrough.

In FIG. 14A, it can be seen that the outer introducer sleeve 552 has a distal portion 565 that is fabricated of a spring material that defines a plurality of spring struts 566 and openings 568 to allow movement of the structure 560 from the repose position of FIG. 14A to the tensioned position of FIG. 14B. In one variation, the struts 566 define triangular shapes around openings 568 and the struts can range in number from about 4 to 20 or more. In a typical embodiment, the struts 566 are fabricated by cutting a thin-wall tubing of a spring material (typically but not necessarily formed integrally with the outer introducer sleeve 552) and then forming the struts 566 into the repose shape as shown in FIG. 14A, e.g. by heat treatment over a mandrel or the like. In another embodiment, the struts can be formed from a round, flat or oval spring-type wire elements. The wire elements then can be welded or otherwise bonded to the distal end 570 of the rigid sleeve portion indicated at 572. As shown in FIGS. 14A and 14B, the resilient structure 560 comprises a zig-zag ring having a plurality of distal apices and proximal apices wherein the proximal apices are joined to a base ring attached to the distal end 558 on the outer tube.

As can be further seen in FIGS. 14A and 14B, the resilient structure further comprises an elastomeric material 575, such as silicone, molded over the struts 566. The distal end 570 of the rigid sleeve portion 572 is provided with apertures 578 therein for engaging the over-molded polymer. In one variation, the polymer 575 is a substantially transparent material to allow viewing therethrough. In other variations, the polymer material may be opaque or non-transparent. The tapered shape of the resilient structure 560 in FIG. 14A is configured with a distal opening 580 that has a selected dimension that may range from 10% to 50% of the diameter of the opening 580' of the structure 560 in its expanded shape as shown in FIG. 14B. The dimension of the distal opening 580 in the tapered position of FIG. 14A is selected to allow viewing through the endoscope 545 during insertion of the distal end of the device 500 through a body passageway.

As can be seen in FIGS. 14A and 14B, in one variation the endoscope 545 can be in a proximal position when the resilient structure 560 is in its contracted, tapered configuration and then the endoscope can be move distally when the resilient structure 560 is in its open, tensioned position as shown in FIG. 14B.

Figure 17:
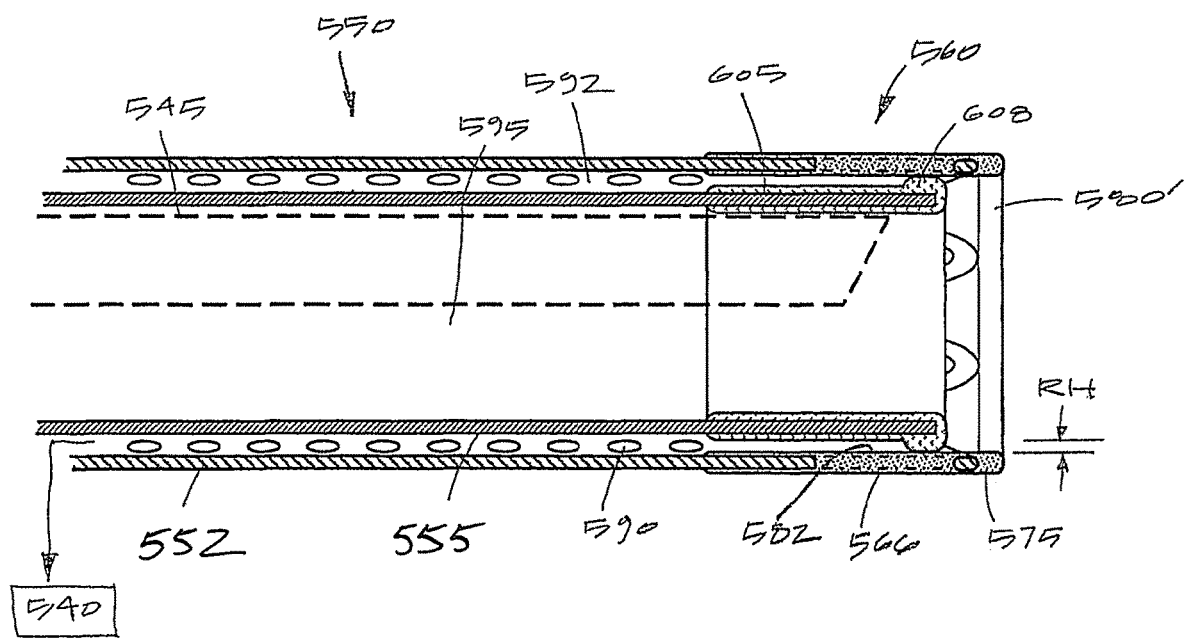
FIG. 17 is a sectional view of the distal end portion of the resecting device and resilient structure of FIG. 14B taken along line 17-17 of FIG. 14B.

FIG. 17 shows the mechanism for moving the resilient structure 560 from the tapered, contracted position of FIG. 14A to the cylindrical position of FIG. 14B. It can be seen that the introducer sleeve assembly 550 includes the inner sleeve 555 that is adapted to move axially from a retracted position to the extended position as shown in FIGS. 14B and 17. In other words, the distal movement of the inner sleeve 555 will contact the inner surfaces 582 of the struts 566 and elastomeric material 575 in the tapered position of FIG. 14A and then push the struts 566 outwardly and stretch the elastomeric material 575 to provide the cylindrical shape of FIGS. 14B and 17 as the inner sleeve 555 is fully extended. FIG. 14B shows that the stroke ST of inner sleeve 555 can range from about 5 mm to 20 mm in a typical embodiment.

Returning to FIG. 13, the mechanism for moving the inner sleeve 555 from its retracted position to its extended position of FIG. 17 can be understood. In FIG. 13, it can be seen that a rotating actuator element 585 is provided which has a cam surface which interfaces with the inner sleeve 555 to move such inner sleeve 555 axially back and forth upon rotation of the finger tab 586. Thus, the finger tab 586 can be designed to move from about 45° to about 90° to move the inner sleeve 555 in the desired stroke ST as shown in FIG. 14B.

Now turning again to FIG. 14A, in another aspect of the invention, the outer introducer sleeve 552 is configured with a plurality of ports 590 which communicate with the annular space 592 between the outer sleeve 552 and the inner sleeve 555 (see FIG. 17). The annular space 592 between the inner and outer sleeves 552, 555 communicates with the negative pressure source 540 and thus provides an outflow path for distention fluid which is independent of the flow channel through the resection component 515 (see FIG. 15). In the variation shown in FIGS. 14A and 16, the device shaft 505 has a fluid inflow channel 595 that comprises the space outward of the shaft 510 of the resecting component 515 and the sleeve 600 carrying the pressure sensing channel 548 as in previous embodiments.

In FIG. 17, it can be seen that the distal portion of the inner sleeve 555 includes a polymer (e.g., silicone) over-molded portion 605 which serves two purposes. First, the polymer over-molded portion 605 has an annular ridge 608 which interfaces with the inner surfaces 582 of the struts 566 and elastomeric material 575. The radial height RH of the annular ridge 608 thus provides the annular space 592 between the outer surface of the inner sleeve 555 and the inner surface of the outer sleeve 552 through which distention fluid may be aspirated after flowing through the multiple ports 590 in the outer sleeve 552. Secondly, the annular ridge 608 of the over-molded polymer portion 605 can be adapted to seal the interface between the inner sleeve 555 and the resilient structure 560 so that distention fluid is not aspirated through the distal opening 580' of the resilient structure 560 in its cylindrical shape as shown in FIG. 17. This aspect of the invention may be useful to prevent and interference with inflows of distention fluid through inflow channel 595 (see FIG. 16). Rather, the variation shown in FIG. 17 allows for fluid inflows to exit the resilient structure 560 and opening 580' around the distal end of the endoscope 545 which provides the advantage of clearing the visual field distal to the endoscope 545 to thereby maintain clear viewing. If both inflows and outflows were adjacent to one another in the interior of the resilient structure 560, the clearing of the visual field with fluid inflows could be impaired. In another variation (not shown), the annular ridge 508 could be provided with notches to allow a portion of the fluid outflows into annular space 592 to flow through the distal opening 580'. In a typical embodiment, the negative pressure source 540 would communicate with both the annular space 592 and the aspiration channel 525 in the resection component 515.

FIG. 15 shows the introducer sleeve assembly 550 and the resilient structure 560 in its expanded position with the working end 512 of the resecting component 515 advanced through the distal the opening 580' in the resilient structure 560. The working end 512 of the resecting component 515 is similar to the previously described embodiments.

Figure 18:
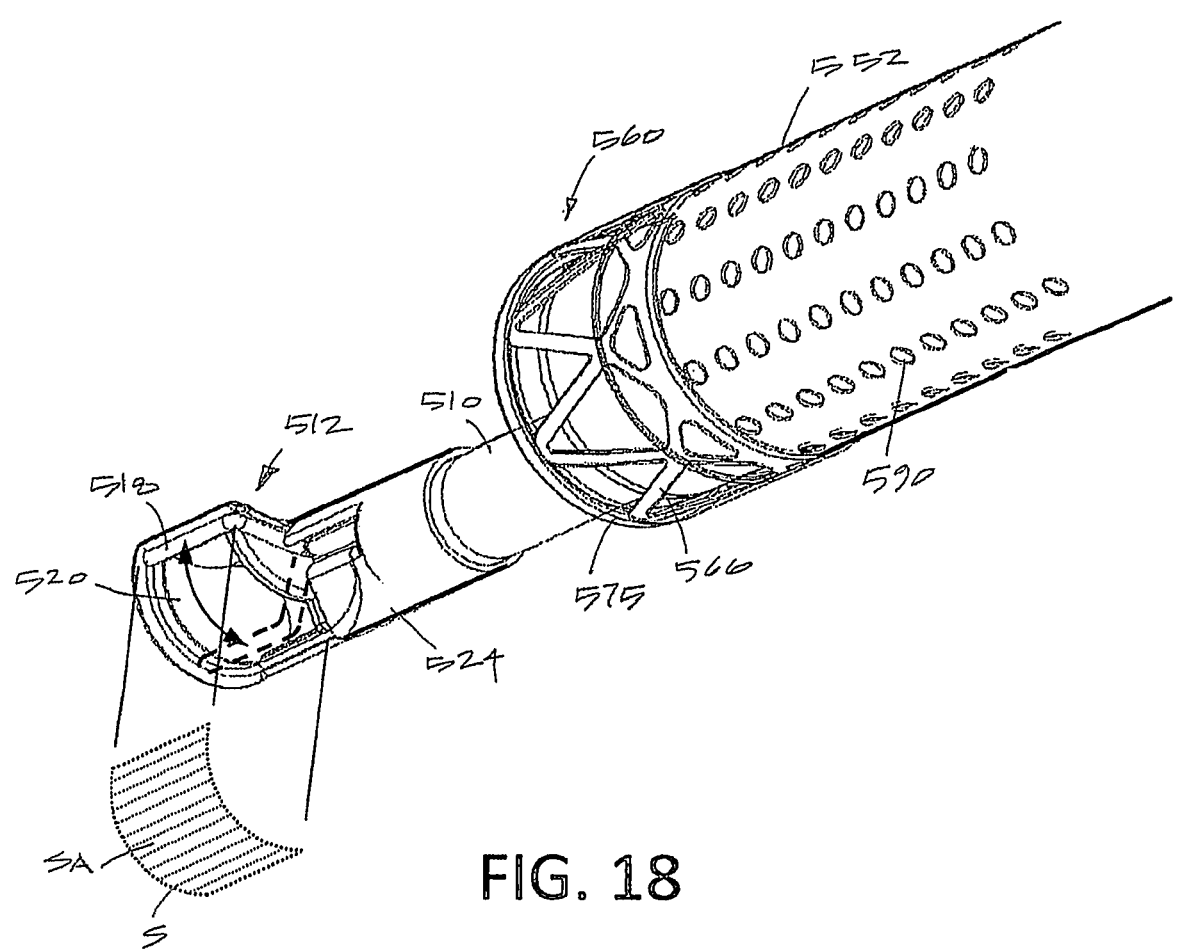
FIG. 18 is a view of the distal end portion of the resecting device of FIG. 15 showing the working end of the resecting component and further illustrating the surface area of the sweep of the oscillating RF electrode.

FIG. 18 shows the distal end of the introducer sleeve assembly 550 and resilient structure 560 and the working end of the resection component 515 from a different angle. In this variation, it can be seen that the window 520 of the working end defines a surface S or curved plane across which the electrode 518 oscillates and cuts tissue. In this variation, the window 520 has a substantially large surface area SA for interfacing with targeted tissue, wherein said surface area can range from 5 mm$^2$ to 40 mm$^2$.

Figure 19:
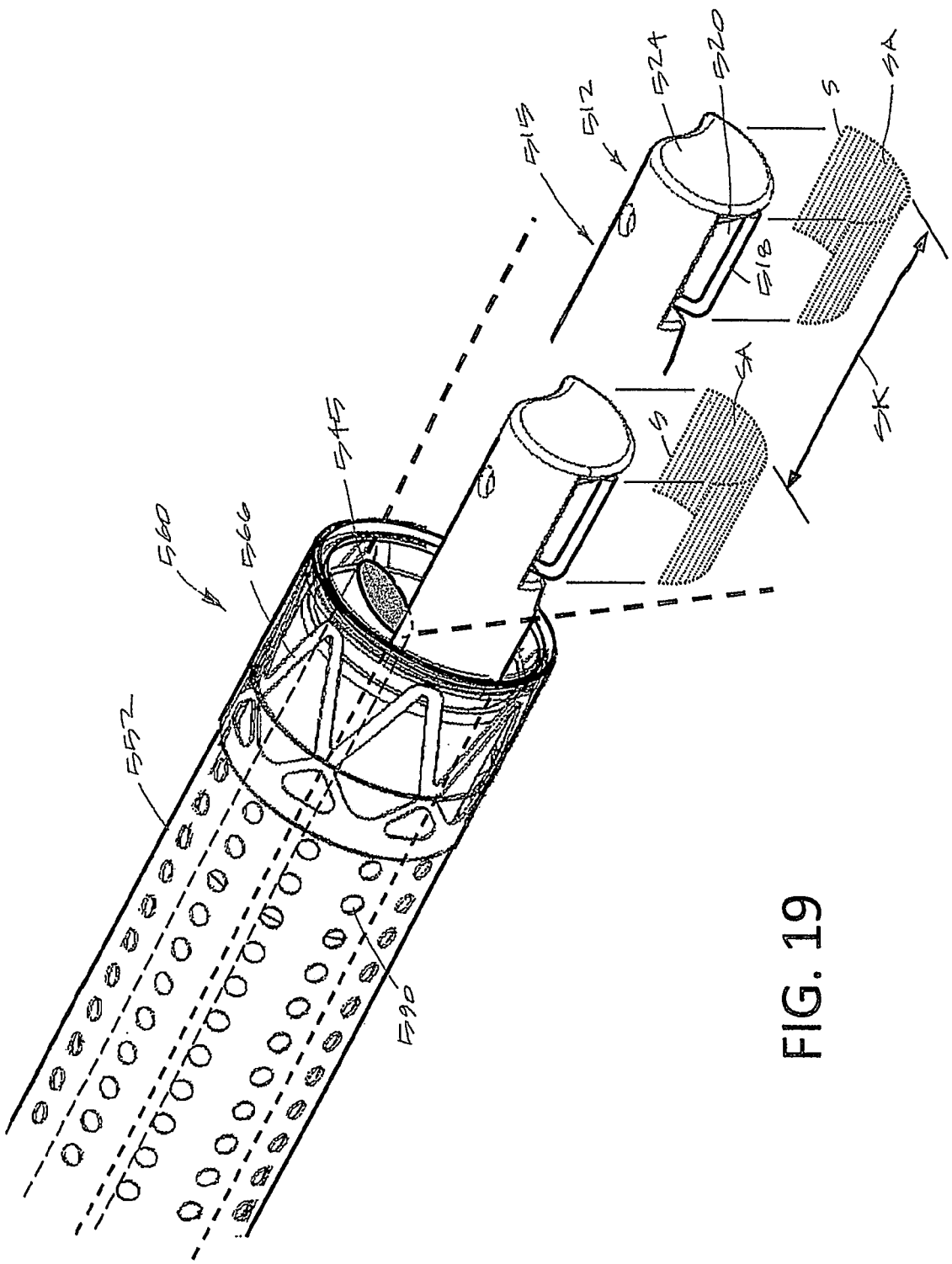
FIG. 19 is another view of the distal end portion of the resecting device of FIG. 18 showing the stroke of the resecting component and again illustrating the surface area of the sweep of the oscillating RF electrode in combination with the stroke.

FIG. 19 shows the working end 512 of the resection component 515 from a different angle and further shows the stroke SK of the resecting component 515 and the surface area SA of the window 520. The stroke SK of the resecting component 512 can range from 5 mm to 20 mm, and typically is from 8 mm to 15 mm. Thus, it can be understood that the area of targeted tissue that interfaces with the electrode 518 over the stroke SK of the resecting component 515 is substantially large, for example from 25 mm$^2$ to 800 mm$^2$. Thus, the oscillating electrode 518 in a typical procedure can provide a tissue removal rate that is greater than 5 grams per minute, and often is greater than 10 grams per minute.

Figure 20:
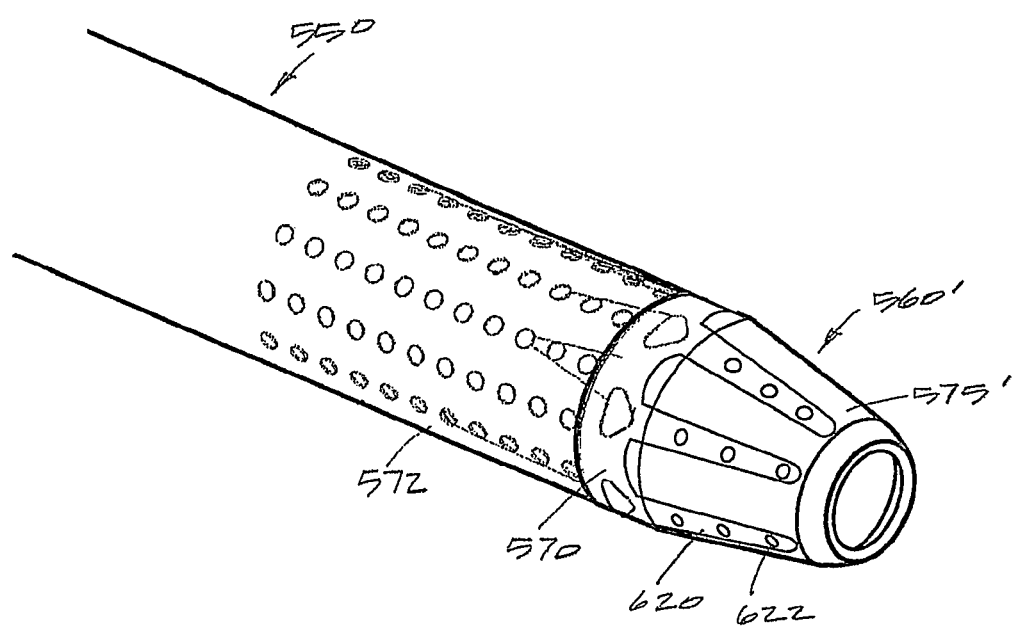
FIG. 20 is a view of the distal end portion of a resecting device similar to that of FIGS. 14A-14B with another variation of a resilient structure having a contracted, tapered shape that can be actuated to an expanded, cylindrical shape.
Figure 22:
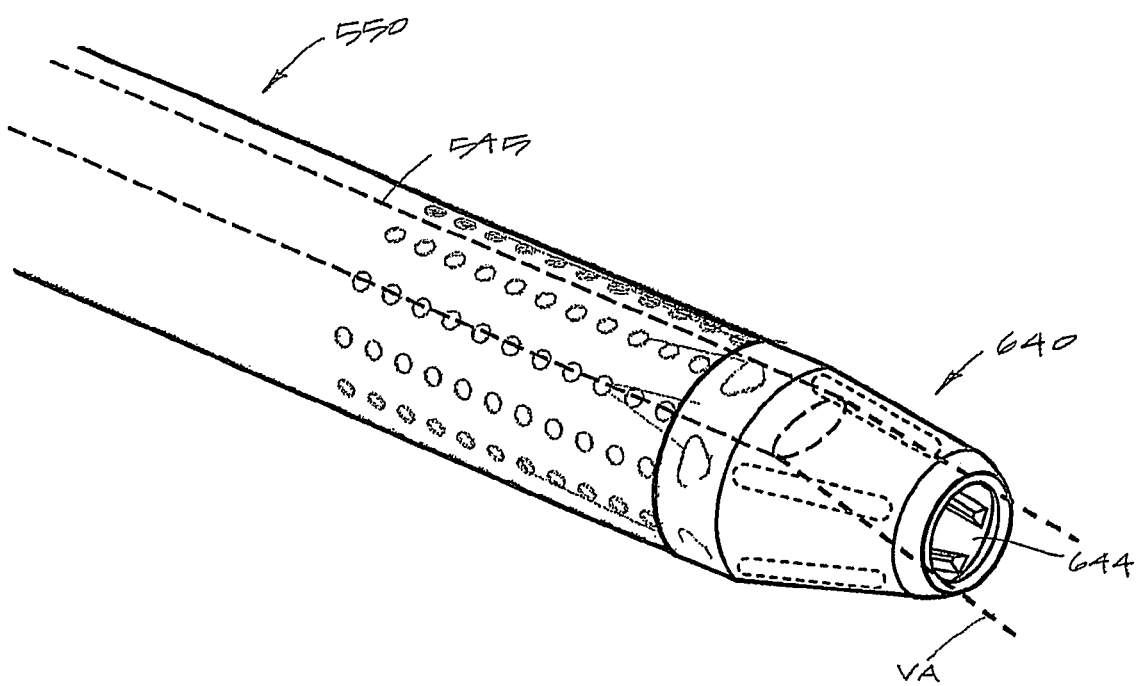
FIG. 22 is a perspective view of the distal end of a resecting device with yet another variation of a resilient structure similar to that of FIG. 21 within asymmetric shape having a distal opening offset from the centerline of the instrument shaft.

Now turning to FIG. 20, another introducer sleeve assembly 550 is shown with a different variation of a resilient structure 560'. In this variation, the resilient structure 560' again has spring-type metal elements 620 extending from the distal end 570 of the rigid sleeve portion 572. The metal elements 620 or struts have a linear shape rather than the triangular as in the previous embodiment. Such elements 620 are flexible to move and deform between the tapered shape as shown in FIG. 22 and an expanded, cylindrical shape that stretches the elastomeric material 575' as in FIG. 14B. In one variation, the metal elements 620 have apertures 622 therein or other features to engage the over-molded elastomeric material 575'. It is necessary to secure the over-molded elastomer to the metal elements 620 to prevent axial stretching of the resilient structure 560' as the inner sleeve 555 (FIG. 17) is advanced distally to its extended position that might otherwise axially stretch the elastomer 575'. In use, the resilient structure of FIG. 20 can be actuated from the tapered shape of FIG. 20 to its open, cylindrical shape by extension of inner sleeve 555 as shown previously in FIG. 17. The open shape alternatively can be oval, elliptical, polygonal or any combination thereof which is enlarged to allow for endoscopic viewing the passage of the resection device therethrough.

Figure 21:
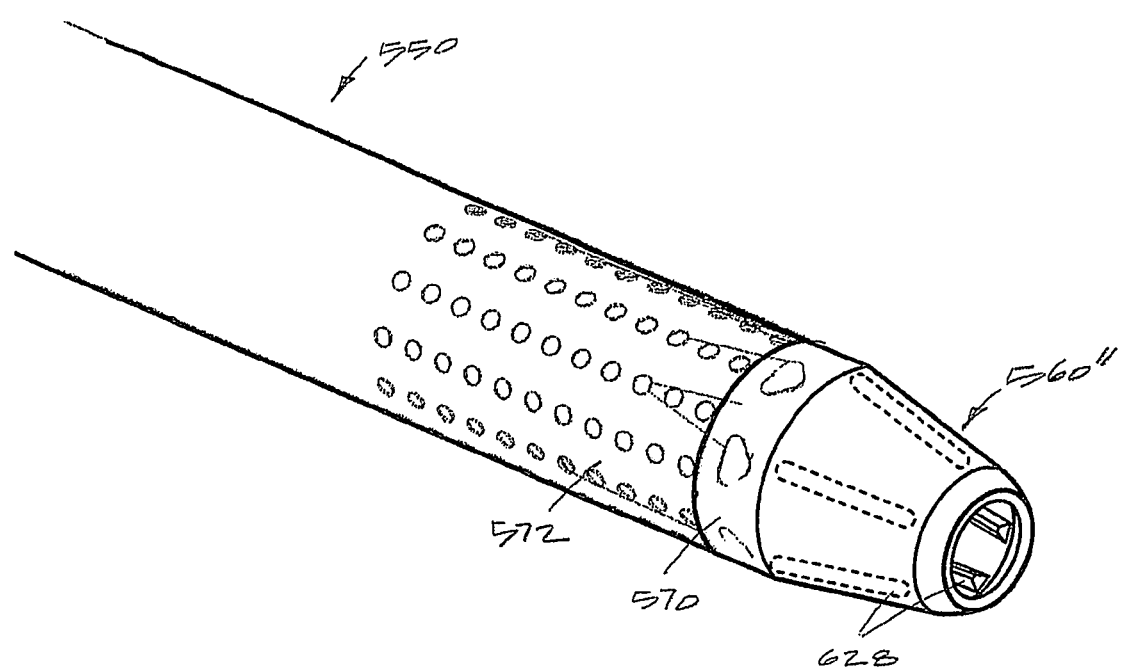
FIG. 21 is a perspective view of the distal end of a resecting device with another variation of a resilient structure similar to that of FIG. 20.

FIG. 21 shows another variation of a resilient structure 560" which is similar to that of FIG. 20 except that there are no spring-type metal elements extending distally from the distal end 570 of the rigid sleeve portion 572. In this variation, the entire resilient structure 560" is a molded polymer such as silicone that includes non-stretchable interior ribs 628 that prevent the resilient structure 560" from being stretched axially when the inner sleeve 555 is extended. In this variation, the inner sleeve 555 would have a polymer over-molded tip section similar to that shown in FIG. 17. However, in this embodiment, an annular ridge similar to ridge 608 and FIG. 17 would be provided with notches therein to interface with each of the non-stretchable ribs 628. In all other respects, the variation of FIG. 21 would function as the variation shown in FIGS. 14A and 14B.

FIG. 22 is another variation of resilient structure 640 that is similar to that of FIG. 21 except that the structure 640 is asymmetric with the distal opening 644 being off-center relative to the central axis of the sleeve assembly 550. In this variation, the distal opening 644 would be configured to be optimally aligned with the field of view of the endoscope 545 so as to improve the viewing angle VA through the opening 644 when the resilient structure 640 is in the tapered position of FIG. 22. This variation would be moved from the tapered shape of FIG. 22 to an open, cylindrical shape by extending the inner sleeve 555 as described previously.

While the introducer sleeve assemblies of FIGS. 14A-14B and FIGS. 20-22 have been described as integrated with a resection device 515, it should be appreciated that the concentric sleeve assembly 550 and tapered resilient structure 560 can comprise an independent introducer device with an endoscope 545 for visual access to any body cavity or potential space with such an introducer and optional irrigation.

While the variations of the expandable distal end are described above as including an elastomeric material, it is also possible to provide an introducer distal end that has overlapping metal leaves similar to that of a camera shutter that can be moved from a tapered shape to a non-tapered shape. Further, in various embodiments that utilize metal struts embedded in an elastomeric material, such metal struts may be of a spring material and be tensioned in either the tapered or non-tapered shape with the elastomeric material responsible for providing the repose tapered shape of the structure.

Figure 23:
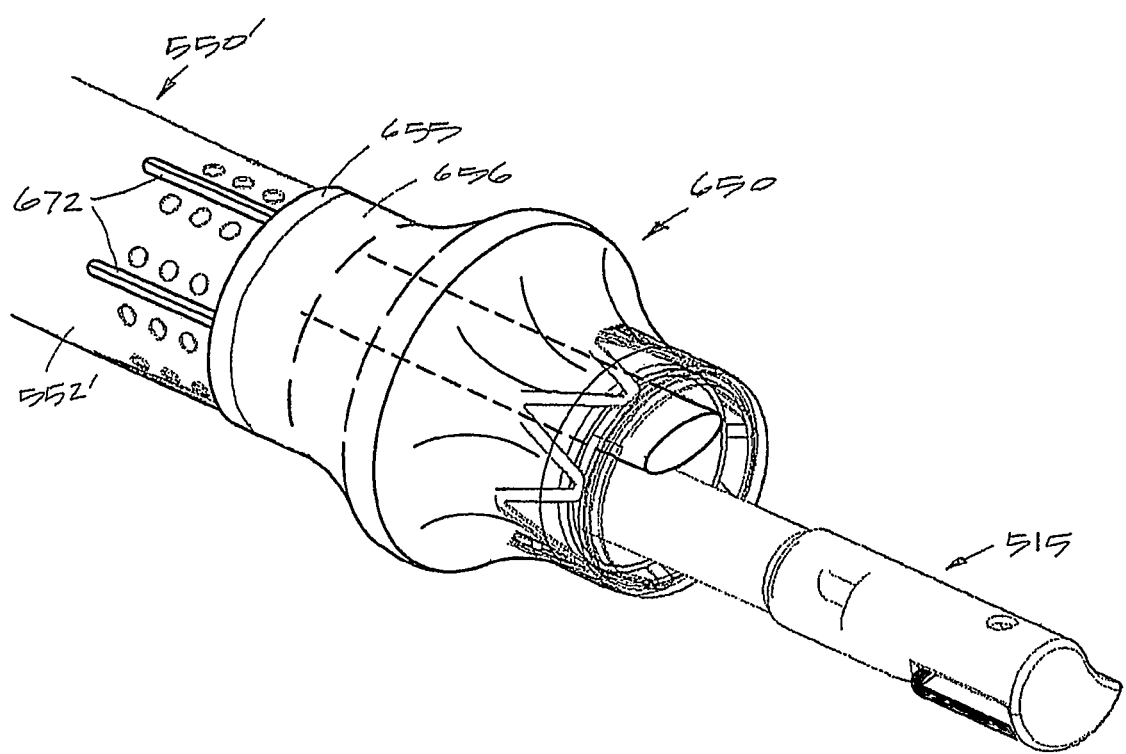
FIG. 23 is a perspective view of the distal end of another variation of a resilient structure similar to that of FIGS. 14A-14B which includes an additional elastomeric structure that is deformable to provide an expanded annular shape for sealing a body passageway.
Figure 24:
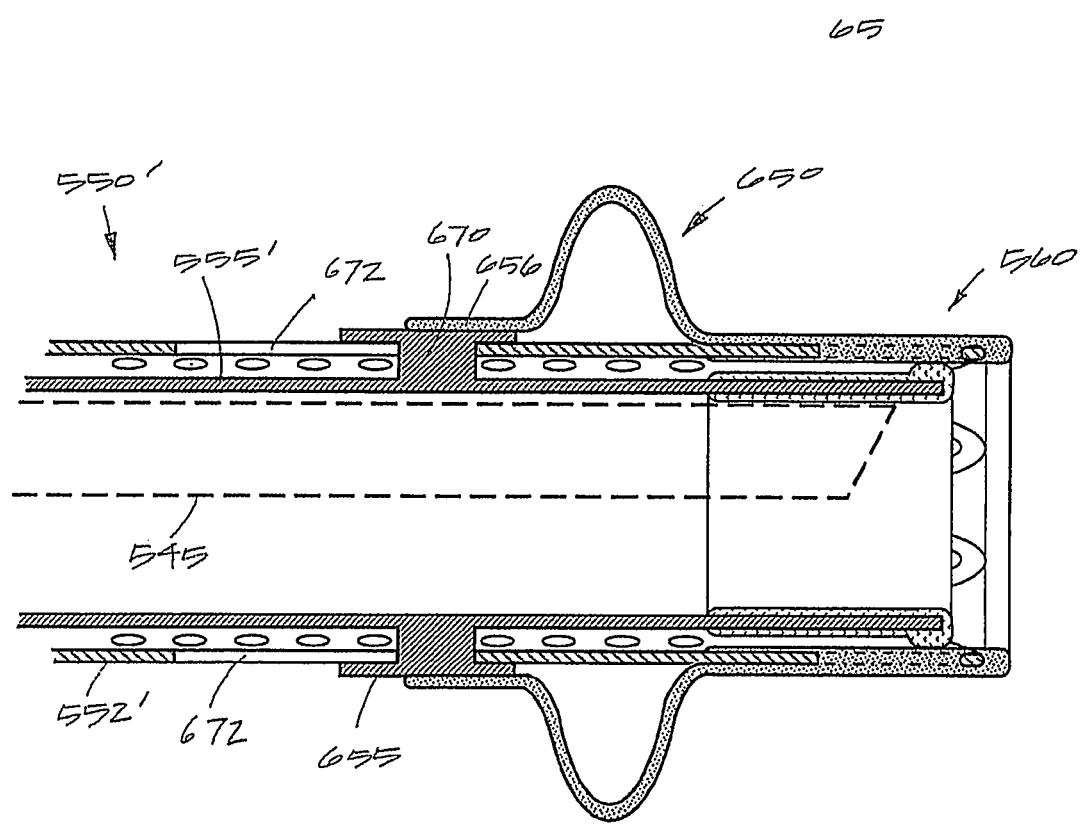
FIG. 24 is a sectional view of the resilient structure of FIG. 23 with the elastomeric structure deformed to an expanded annular shape.

FIGS. 23 and 24 illustrate another variation which is similar to that of FIGS. 14A, 14B and 15 except the distal end of sleeve assembly 550' carries a deformable elastomeric portion 650 that can be actuated to in an expanded configuration to function as a seal in a body lumen. As can be understood from FIGS. 23 and 24, the extension of the inner sleeve 555' within outer sleeve 552' causes the elastomeric portion 650 to buckle upward to provide and annular sealing structure. It can be seen that inner sleeve 555' is coupled to an outer collar 655 that is attached to the proximal end 656 of the elastomeric portion 650. In one variation, the elastomeric portion 650 is an integral part of the resilient structure 560. The inner sleeve 555' is coupled to the outer collar 655 by elements 670 that slide in slots 672 in the outer sleeve 552'. Thus, the movement of the inner sleeve 555' is adapted to cause both movement of the resilient structure 560 from the tapered shape to the non-tapered shape (FIGS. 14A-14B) as well as movement of the elastomeric component 650 to the expanded shape of FIGS. 23-24 for sealing a body passageway.

Figure 16:
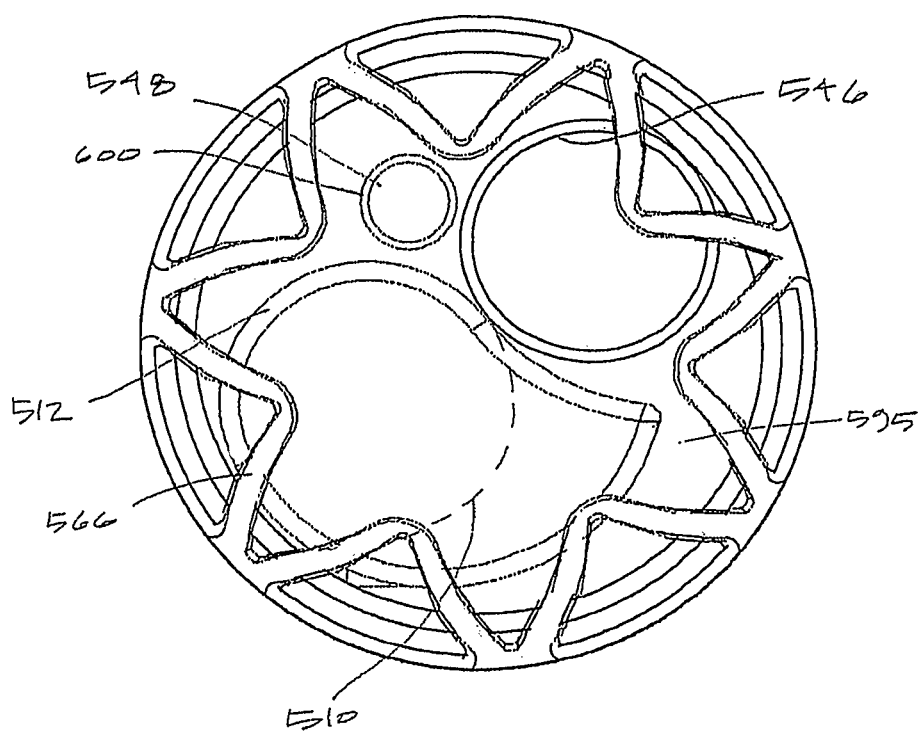
FIG. 16 is an end view of the distal end portion of the resilient structure of FIG. 14B showing various flow channels therein.

In another variation, some or all of the inner and outer surfaces of sleeves and structures in the interior of the sleeve assembly 550 as shown in FIGS. 14A, 16 and 17 can be coated with a dielectric material that can withstand high temperatures so as not to interfere with the operation of the resection device 515.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A medical device comprising:
    a handle;
    an elongated tubular member adapted for introduction into a body lumen of a patient;
    a central passageway within a distal portion of the tubular member;
    a treatment tool that is extendable and retractable from the central passageway;
    an imaging device disposed in the central passageway; and
    an atraumatic tip coupled to a distal portion of the tubular member, said atraumatic tip having a tapered configuration for introduction in the body lumen and a non-tapered configuration to allow extension of the treatment tool distally from the tubular member, and where the atraumatic tip comprises a frame structure formed of a shape memory material having a conical shape memory to provide the tapered configuration and expendable to a cylindrical shape to provide the non-tapered configuration;
    wherein the elongated tubular member comprises an outer tube and an inner tube carried in an interior lumen of the outer tube and wherein the frame structure is coupled to a distal end of the outer tube; and
    wherein an annular space between an inner surface of the outer tube and an outer surface of the inner tube of the elongated tubular member is configured to be coupled to a negative pressure source via the handle.

2. The medical device of claim 1, further comprising an elastomeric material disposed over the frame structure.

3. The medical device of claim 2, wherein the frame is embedded in the elastomeric material.

4. The medical device of claim 2, wherein the elastomeric material is substantially transparent.

5. The medical device of claim 1, wherein atraumatic tip is moved from the tapered configuration to the non-tapered configuration by relative axial movement of the inner tube and outer tube.

6. The medical device of claim 5, wherein the central passageway tapers to a distal port having a lesser diameter in its tapered configuration than in its non-tapered configuration.

7. The medical device of claim 1, wherein a distal portion of the outer tube is perforated.

8. The medical device of claim 1, wherein the tubular member includes an interior channel communicating with a fluid inflow source.

9. The medical device of claim 1, wherein the tubular member includes an interior channel communicating with a pressure sensor.

10. The medical device of claim 1, further comprising an actuator in the handle for causing relative axial movement of the inner tube and outer tube.

11. The medical device of claim 1, wherein the frame structure comprises a zig-zag structure with a plurality of struts joined at distal apices and proximal apices wherein the proximal apices are joined to a base ring attached to the distal end of the outer tube.

12. The medical device of claim 1, wherein the tool is an RF surgical tool.

* * * * *